United States Patent [19]
Morozov et al.

[11] Patent Number: 6,033,913
[45] Date of Patent: Mar. 7, 2000

[54] DETECTION OF LIGAND INTERACTION WITH POLYMERIC MATERIAL

[75] Inventors: Victor Morozov; Tamara Morozova, both of New York, N.Y.

[73] Assignee: New York University, New York, N.Y.

[21] Appl. No.: 08/879,513

[22] Filed: Jun. 20, 1997

Related U.S. Application Data

[60] Provisional application No. 60/028,147, Jun. 20, 1996.

[51] Int. Cl.[7] .................................................... G01N 33/48
[52] U.S. Cl. ................................ 436/86; 73/1.79; 73/794; 73/795; 73/826; 73/833
[58] Field of Search ........................ 436/86–90; 73/1.79, 73/769, 794–795, 826, 833

[56] References Cited

U.S. PATENT DOCUMENTS

| | | |
|---|---|---|
| 4,114,420 | 9/1978 | Browning . |
| 5,510,481 | 4/1996 | Bednarski et al. . |

FOREIGN PATENT DOCUMENTS

| | | |
|---|---|---|
| 0121385 | 10/1984 | European Pat. Off. . |
| 0 402 917 | 12/1990 | European Pat. Off. . |
| 55-156834 | 12/1980 | Japan . |
| 58-182540 | 10/1983 | Japan . |
| 8905977 | 6/1989 | WIPO . |
| WO 94/02852 | 2/1994 | WIPO . |
| WO 94/28372 | 12/1994 | WIPO . |

OTHER PUBLICATIONS

Berry, B.S. et al., "Bending–cantilever method for the study of moisture swelling in polymers.", IBM Journal of Research and Development, vol. 28, No. 6, pp. 662–667 (1984).

Morozov, Victor et al., "Mechanical detection of interaction of small specific ligands with proteins and DNA in cross–linked samples.", Analytical Biochemistry, vol. 201, pp. 68–79 (1992).

*Primary Examiner*—Lyle A. Alexander
*Attorney, Agent, or Firm*—Browdy and Neimark

[57] ABSTRACT

A method and apparatus for measuring ligand binding to DNA or protein uses changes in the mechanical properties of strips of the DNA or protein to detect the formation of ligand complexes. Samples strips are prepared by pouring protein solution onto a glass surface, drying the solution, and causing the protein to be cross-linked; the cross-linked film is scraped off, cut into strips, and mounted in the stress/strain measuring apparatus, which includes force and strain transducers. The sample is held by arms and can be immersed into solutions. The arms are attached to transducers. The apparatus includes a sample holder. The sample films may include end reinforcements and may be pinned or glued to the arms.

44 Claims, 28 Drawing Sheets

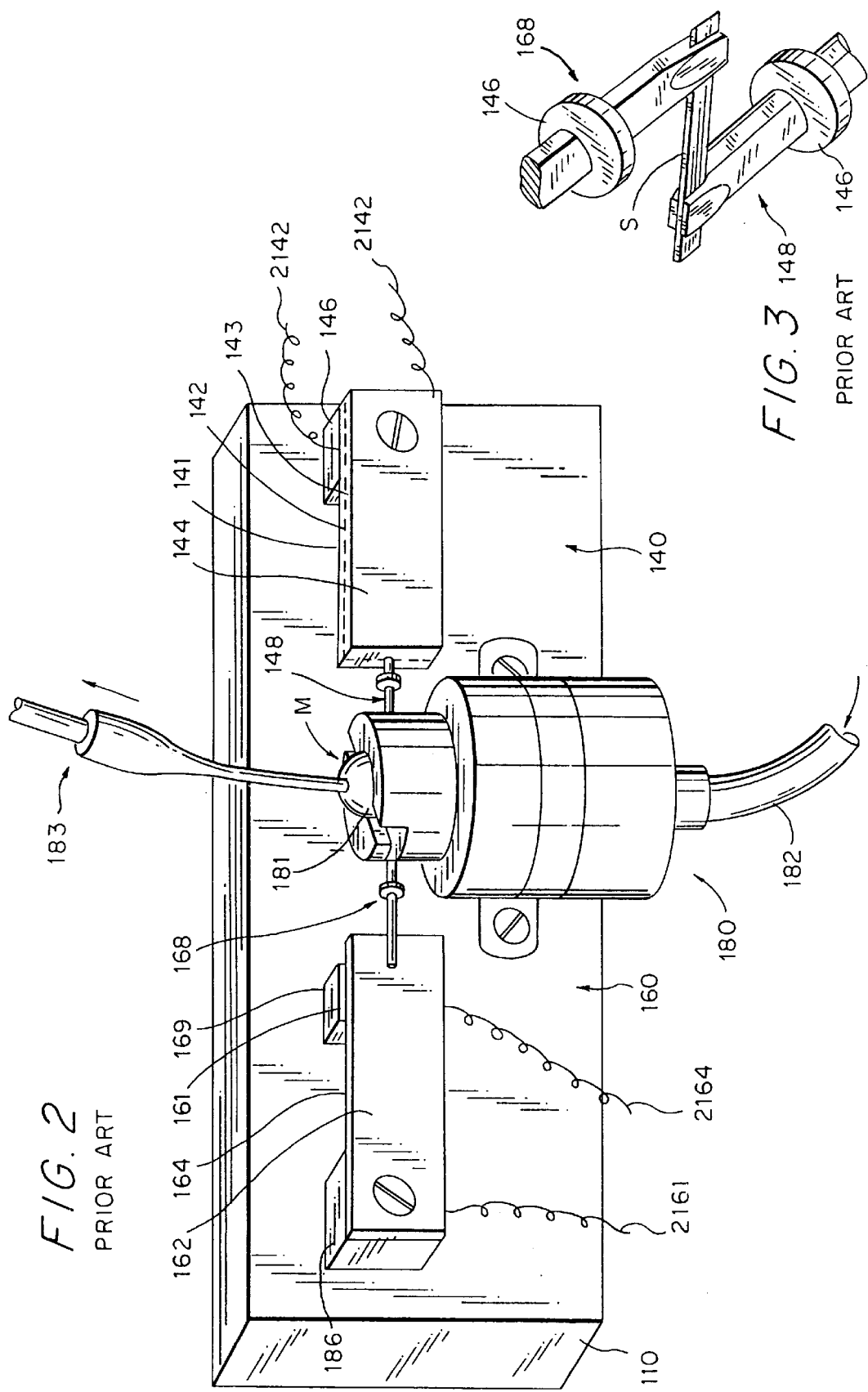

FIG. 21
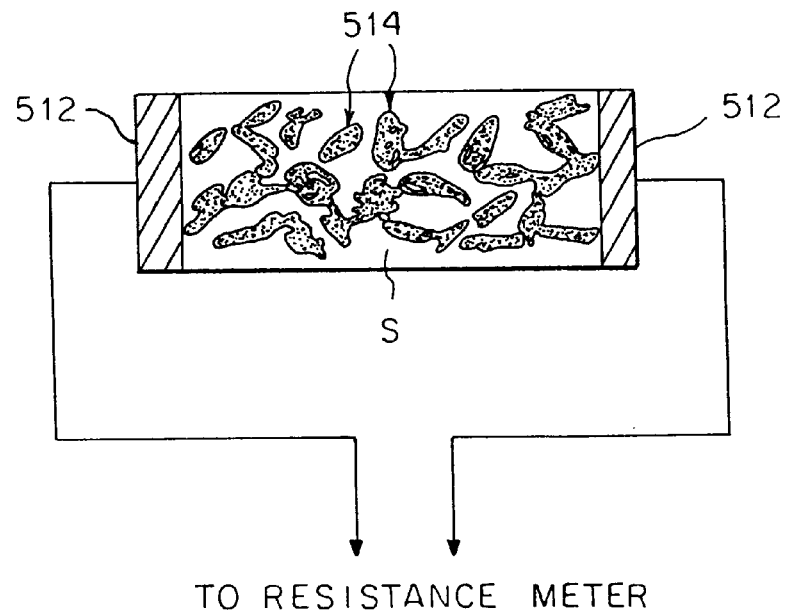
TO RESISTANCE METER
↓ LIGAND BINDING
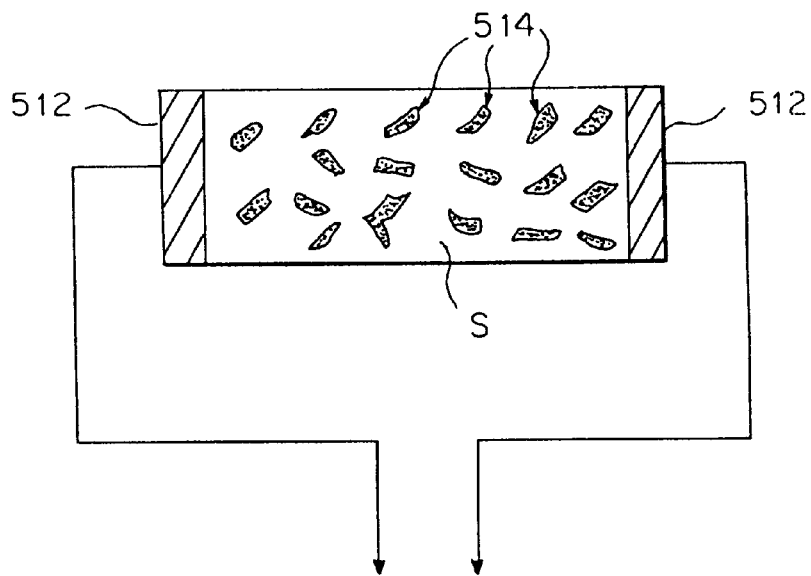

DETECTION OF LIGAND INTERACTION WITH POLYMERIC MATERIAL

CROSS-REFERENCE TO RELATED APPLICATIONS

The present application is a non-provisional application claiming benefit under 35 U.S.C. §119(e) of provisional application Ser. No. 60/028,147, filed Jun. 20, 1996, the entire contents of which are hereby incorporated herein by reference.

FIELD OF THE INVENTION

The present invention relates to methods and apparatus for determination of ligand interaction with macromolecules such as proteins and DNA.

BACKGROUND OF THE INVENTION

Studies of the interaction of proteins or DNA with small ligands are commonplace in biochemical, pharmacologic, and toxicological research. To detect the interaction of macromolecules with their specific ligands in solution, one can either measure binding-induced changes in physical properties of the macromolecule or of the ligand (optical, NMR, etc.) or use some partitioning technique (equilibrium dialysis, size-exclusion chromatography, etc.). Each of these approaches has serious limitations. For example, the optical properties of a macromolecule will change only if some reporter group (fluorescent or absorbent) is by chance situated near the binding site. On the other hand, partitioning methods require the determination of small concentrations of ligands, which often necessitates synthetic attachment of radioactive or chromogenic labels. This makes the procedure expensive, tedious, and time consuming. Some of these negative features have been avoided recently by the use of titration calorimetry. Nevertheless, in research on a large series of ligands, considerable consumption of protein and DNA in solution may be a disadvantage to all these methods.

To explain further: Assays of protein specificity can also be classified according to how they are performed-either in solution (homogenous assays) or in a heterogeneous system, in which the protein or specific ligand is immobilized (heterogeneous assays). The performance characteristics, advantages and disadvantages of all these methods, are determined primarily by the detection technique used.

In homogeneous methods, binding of a ligand to a protein is detected by a physical (mostly optical) method. With few exceptions, homogeneous methods are not universal, since only binding accompanied by large conformational changes in proteins or binding with sites having a neighboring reporter group can be reliably detected. Microcalorimetry and equilibrium dialysis are examples of more general homogeneous methods. However, the former requires relatively large quantities of proteins for each assay; since protein samples are not reusable, screening by this method is material consuming. On the other hand, equilibrium dialysis is slow and requires sensitive methods for determining ligand concentrations if small amounts of protein are used.

Heterogeneous methods are more economical, in that they require much less protein for each sample and the protein sample can be reused. Binding in heterogeneous systems can be detected either directly by changes in physical properties of a protein layer (mass, optical properties, etc.), or indirectly, by competitive replacement of a labeled ligand by a substance under study. Direct methods can identify binding to any site in a protein, whereas indirect methods detect binding at known sites, overlooking ligand binding at secondary sites. This is why indirect heterogeneous methods cannot be used for primary screening of a protein with unknown function or binding site.

Heterogeneous methods encounter serious difficulties in analysis of binding of small ligands (Karlsson, R., *Analyt. Biochem.*, 221:142–151 (1994)). For direct methods, this is due to the fact that small changes in mass and in optical properties of protein layer accompanying binding of small ligands are involved. In indirect methods, labeling of small ligands themselves presents a problem, since introduction of a fluorophore or enzyme label might alter the specificity of the labeled ligand. Radioactive labeling is free of this drawback, although it is considered to be dangerous and expensive, since radioactive ligands for each protein must be available.

The present inventors originated a mechanochemical method of using the mechanical elastic characteristics of a protein film to measure ligand-protein interaction. The method is described in two publications: V. N. Morozov and T. Ya. Morozova (1992) "Mechanical Detection of Interaction of Small Specific Ligands with Proteins and DNA in Cross-Linked Samples", *Analytical Biochem.*, 201:68–79; and in V. N. Morozov and T. Ya. Morozova (1984) "Protein Molecule as a Bioanalytical Device", *FEBS Letters*, 175:299–302, the entire contents of both of which are hereby incorporated herein by reference.

In those articles, the inventors disclosed a new method for detecting the interaction of macromolecules with their specific ligands by exploiting the ability of cross-linked protein and DNA solid and gel samples to change their mechanical properties upon binding of the specific ligands with the macromolecules. This mechanochemical phenomenon was initially discovered in lysozyme crystals (Morozov et al, *J. Mol. Biol.*, 157:173–179 (1982), Morozov et al, *Biophysics (Sov.)*, 28:786–793 (1983)) and in papain films (Morozov et al, *FEBS Lett.*, 175:299–302 (1984)). The inventors suggested that the phenomenon has some universal character because it is based on two well-known facts. First, many crystalline proteins retain their ability to bind specific ligands. This fact is widely used in the X-ray analysis of protein-ligand complexes (Rupley in *Structure and Stability of Biological Macromolecules*, Timasheff and Fasman, Eds., pp. 291–353, Dekker, New York (1969)). Second, whatever the character of this binding, to some extent it changes inter- and intramolecular interactions, the molecular structure, and the packing of molecules in the solid sample.

Of all the physical parameters of protein solids, the mechanical ones seem to be the most sensitive to these changes. Theoretical analysis shows that deformation of protein molecules by $10^{-6}$ Å can be, in principle, measured with mechanical methods. In practice, changes in average protein dimensions of $10^{-2}$ Å can be readily detected.

In order to prepare samples for mechanochemical testing, the inventors used a process shown in FIG. 1. A salt-free solution (10–200 mg/ml of protein) was poured onto a glass plate and rapidly dried under a reduced atmospheric pressure of 10–15 mm Hg. The resulting dry protein film (5–10 $\mu$m thick) was then cross-linked in a vapor of 25% glutaraldehyde (GA) solution at 25–27° C. The time required to obtain insoluble film varied between 0.5 and 6 h for different proteins. The cross-linked film was washed with water, to remove the excess aldehyde, and then carefully detached from the glass plate.

DNA films were prepared by dialyzing a DNA precipitate in alcohol against a 10 mM NaCl solution to give a gel with a DNA concentration of about 100 mg/ml. The gel was then distributed over the glass surface, dried as described for protein films, and cross-linked by UV irradiation under a 30 W germicidal lamp located 0.1 m from the sample for 1.5 h (Sheldon et al, *Proc. Natl. Acad. Sci. USA*, 62:417–421 (1972)).

Strips 300–700 µm long and 20–50 µm wide were cut with a razor blade to be used as samples. These samples were then mechanically tested while immersed in a ligand solution. The mechanical testing involved stretching the strip lengthwise, letting it relax under isometric condition and then measuring changes in isometric tension in response to immersing the sample into ligand solutions.

In their prototype method, the inventors employed an apparatus that is shown in FIG. 2, a partly schematic view labeled "prior art". The apparatus uses two devices to stretch the sample. One is a bimorph type transducer, used mostly to periodically stretch the sample when measuring its elastic modulus. Because practical deformation of piezomaterials under dc voltage is not large enough and not stable enough, another device is used to apply constant strain and to keep it precisely isometric during testing. This is done by a rotating quartz plate (105 in FIG. 5; not shown in FIG. 2). Thus, the apparatus uses a rotating quartz plate and piezoelectric bimorph to stretch the prepared strip in static and dynamic ways respectively and a variable-capacitance transducer to measure the static and dynamic stresses in the sample in response to the deformations and ligand applications.

Connected to a bedplate or base 110 are a flow chamber 180, strain transducer 140, and force transducer 160. The flow chamber 180 includes a well 181 full of ligand solution, which is held in the well by gravity and surface tension. The solution in the open top of the well 181 is bounded by a meniscus M. The solution is fed into the well 181 through a pipe 182 and is sucked off the top of the meniscus M by a suction tube 183. Inside the meniscus M and the sides of the well 181 is a sample strip S held by pincers 168 and 148, which are attached to their respective transducers. Flow chamber 180 is mounted on the device housing and is capable of moving up and down, thus enabling dipping the pincers into chamber (in up position) and enabling an easy access to the pincers (on sample attachment) in down position. The pincers 168 and 148 pass through L-shaped slots in opposite sides of the well 181, so that the pincers are free to move over restricted ranges before they contact the sides of the well 181. The strip mounting and pincers 168, 148 are described more fully below in regard to FIG. 3.

Still considering FIG. 2, the strain transducer 140 includes a rectangular member mounted on the base 110 by a mounting bracket 146. This rectangular member is a piezoelectric bimorph, that is, a sandwich of two layers of piezoelectric material 142 and 143 which are oriented at 180 degrees to one another in such a way that, when an electric field is applied across the sandwich 142/143, one of the layers contracts along the member's length and the other layer expands. As in a bi-metallic thermostat, when one layer expands and the other contracts the member as a whole bends. To apply the electric field needed to bend the sandwich 142/143, both sides of the sandwich member are coated with metal. A metal layer 141 is coated on the underside of piezo layer 142, and a metal layer 144 is coated on the top side of piezo layer 143. Leads 2142 and 2143 connect the metal layers 142 and 144 respectively to an adjustable voltage source (not shown in FIG. 2). By adjusting the applied voltage, the pincer 148 can be moved a calibrated amount.

FIG. 3, also labeled "prior art", shows how the pincers 168 and 148 are connected within the well 181. In each of the pincers 168, 148 the strip S is held by pliers-like pincer jaws formed by splitting a tungsten wire; the split wires are tightened onto the sample S by a sliding ring 146.

The pincer 168 is firmly attached to a resilient cantilevered beam 162, which is mounted on the base plate 110 by a bracket 166. When the strip S in the well 181 is moved by the transducer 140, the beam 162 is deflected by a certain amount; due to this deflection, the beam 162 exerts a restoring force that is a function of its deflection. Therefore, by measuring the deflection of the beam 162 the force or stress in the sample S can be measured. To measure the beam deflection a capacitor is formed as follows: the underside of the beam 162 is coated with a first layer of metal 164 and a block 169, mounted on the base 110, is covered with a second layer of metal 161.

The metal layers 161 and 164 form a parallel-plate capacitor whose capacitance varies with the gap between the metal layers 161, 164; that is, with the deflection of the beam 162, which deflection is proportional to the force in the strip S, within a fraction of a percent. The metal layers 161, 164 are connected by leads 2161, 2164 to circuitry (not shown) which measures the capacitance of the layers electronically (for example, by measuring the frequency of an LC resonant circuit which includes the beam 162 capacitor as the C value and a remote inductor as the L value). The measured capacitance is thus a measure of the tensile force along the strip S.

It is to be noted that the displacement of the pincer 148 is equal to the sum of the displacement of the pincer 168 plus the elongation of the strip S.

The inventors' prototype method was a substantial advance in the art, being a new method of measuring ligand attachment that allowed new sorts of data to be collected. However, the prototype method of sample preparation and the force/strain measuring apparatus used had various drawbacks.

One drawback was that the very small and fragile samples, only 0.3–0.7 mm long, were difficult to handle and clamp for the stress/strain measurements.

The clamping arrangement shown in FIGS. 2 and 3 was quite awkward to use at the sub-millimeter scale. The flimsy strip S needed to be manipulated with great care. The preparation steps involving scraping and cutting the strips needed to be performed under a stereoscopic microscope, and placing the strips S into the pincer jaws required a micromanipulator. The procedure was very time-consuming.

The prototype apparatus of FIG. 3 is likely to grip the sample unevenly: that is, the jaws are quite likely to grip the sample harder at one point along their length than elsewhere, leading to uneven strain across the width of the sample S when the less tightly-gripped portion slides out. They are also likely to grip the sample at different points along the length, so that the effective length of the sample can be indeterminate or even uneven, in spite of the sample S being gripped with equal force at all points across the width. The pincer jaws may even tear the sample S.

The effective or gripped length of the strip S is one of the quantities that is used to calculate the quantitative data that the inventors' method yields. The quantitative results thus could easily be affected by uneven gripping. (The theory of the method is described below in the Detailed Description of the Invention.)

The bad effects of uneven sample gripping could be eliminated by high-precision jaws, but these would be very expensive and easily damaged; and if they were damaged, the damage would not be apparent.

An additional drawback of the prototype mechanical arrangement is that the offset of the two sets of pincer jaws cause fluid-flow problems. The jaws' vertical insertion movement and horizontal test motions require L-shaped slots in the flow chamber, and a flow chamber with such slots is not able to handle liquids with low surface tension, such as organic solvent solutions or water solutions containing surface active compounds, because these would simply leak out; only liquids which do not "wet" the well 181, and therefore will not run out of the slots, can be used.

Another drawback of the FIG. 2 apparatus is that the capacitive force transducer 160 is ill-protected from moisture, dust, and stray electric fields which can affect its readings.

SUMMARY OF THE INVENTION

Accordingly, the present invention has an object, among others, to overcome deficiencies in the prior art such as noted above.

One particular object of the invention is mechanochemical testing of sample strips without the need for micromanipulation apparatus or microscopic viewing when the strips are mounted into a testing apparatus.

Another object is to provide controlled conditions for sample strip attachment.

A third object is to make sample strip mounting simple and quick.

A fourth object is to provide a mechanochemical testing apparatus having a flow cell that can be used with solutions of surface active compounds and solutions of ligands in organic solvents, by use of a design which does not depend upon surface tension forces of the flow cell liquid.

A fifth object is to provide a mechanochemical testing apparatus having effective protection against moisture and dust, and a stable force transducer.

A sixth object is to provide methods of measuring the deformation, upon ligand binding, of a protein or DNA film which do not include measuring lateral elasticity or lateral tensile properties of the protein or DNA film.

The invention thus provides a method and apparatus for quantitative mechanochemical measurement of ligand binding to protein and DNA along with other methods for determining ligand binding by measuring deformation of a protein or DNA film.

The apparatus is designed for the quantitative measurement of the effect of chemicals on a sample strip of polymeric material in an improved manner. The apparatus includes a pair of supporting members, each with a sample-holding tip at one end thereof, for piercing or becoming adhered to the sample strip of polymeric material. Attached to at least one of the supporting members is a means for applying force to the sample strip held by the tips when in use. Also attached directly or indirectly to the sample strip is a means for measuring changes in a chemical, electrical or mechanical property of the sample strip upon being subjected to a chemical when in use. The force is preferably applied or maintained parallel to the direction of the sample strip between the tips so as to elongate or contract the sample strip. A preferred measurement means is one which measures the displacement of one of the supporting members with respect to the other or for measuring the force required to maintain the tips at a constant displacement. In one embodiment, the force means includes means for oscillatingly varying the elongation of the sample strip.

In a preferred embodiment of the apparatus in accordance with the present invention, the apparatus further includes a fluid containment vessel, such as a tank, and the apparatus includes a mechanism for causing the tips holding the sample strip to immerse the sample strip in the fluid held by the fluid containment vessel. In this manner, the sample strip may be tested while immersed in the fluid in the vessel. The apparatus in another preferred embodiment includes a holder for presenting the sample strip to the tips. The apparatus aligns the sample strip holder to a predetermined position relative to the supporting members so as to facilitate attaching the sample strip to the tips.

The present invention further relates to a method of using this apparatus for the quantitative measurement of the effect of chemicals on a sample strip of polymeric material. In this method, the sample strip of polymeric material is affixed to the sample holding tips of the pair of supporting members so as to hold the sample between the tips. The sample strip is then immersed in a reference fluid and force is applied to the sample strip by the apparatus. A physical (chemical, electrical, optical, magnetic, acoustic, mechanical, etc.) property of the sample strip is then measured by the apparatus. The sample strip is then immersed in a fluid containing the chemical to be tested and the same physical property is remeasured. The effect of the chemical on the polymeric material can be determined by detecting a change in the measured property.

The sample strip of polymeric material is preferably affixed to the tips by piercing the sample with the tips or by adhering the sample to the tips by means of an adhesive.

The method of the present invention is preferably used for the quantitative measurement of ligand binding to a protein or nucleic acid material. Thus, the sample strip is preferably a cross-linked protein or nucleic acid material and the chemical whose effect is being measured is the ligand to be tested for its ability to bind to the protein or nucleic acid material.

The present invention also relates to methods for detecting the interaction of the ligand with a protein or DNA by measuring a physical characteristic which will be affected by the deformation of a cross-linked film of the protein or DNA which occurs upon ligand binding. The protein or DNA to be tested is first cross-linked to form a solid sample strip of the protein or DNA. This sample strip of cross-linked protein or DNA is brought into contact with the ligand of interest. In order to detect any interaction between the protein or DNA and the ligand of interest, a physical characteristic of the sample strip is measured before and after contact of the strip with the ligand. Any method of measurement may be used in which the deformation of the cross-linked structure of the sample strip will be detectable. If any difference between the measured characteristics before and after the strip is brought into contact with the ligand is detected, this will evidence interaction of the ligand with the protein or DNA.

As the specific embodiment of this method involving measuring changes in lateral elasticity of such a cross-linked strip or changes in lateral tensile properties has previously been published by the present inventors, such means of measuring the physical characteristics of the sample strip are expressly excluded from the method of the present invention. By the term "lateral" is meant a property that is measured along the axis corresponding to the longest dimension (length) of the sample film. It should be understood that the methods using measurement of lateral elasticity or lateral tensile properties which are excluded from the method of the present invention are still considered to be part of the present invention when the method uses the novel apparatus of the present invention.

Among the novel methods which may be used to detect ligand interaction with the protein or DNA, other than the measurement of lateral elasticity or lateral tensile properties, include the following. The cross-linked film of protein or DNA may be adhered to a second layer which is not affected by the ligand, in order to form a bimorph structure. The second layer may be made of a strain- or stress-sensitive material (e.g., piezoelectric) or it may be made of the same protein or DNA as the sample strip on which the active cross-linked site has been blocked. Upon ligand-induced deformations in the cross-linked protein or DNA, the whole structure bends, and such bending may be measured by any suitable method, such as optically, electrically, etc. A kind of modified bimorph involves adhering the sample strip to a strain-sensitive surface. Upon deformation of the sample strip, some changes in strain or stress in the sensitive surface will be induced, which can be used to generate an electrical signal in a way similar to that in known tensoresistive sensors.

Another way to practice the method of the present invention is to include particles of a conductive material, such as carbon powder, into the protein or DNA film and then place electrodes on either side of the film. The conductivity of the film is then measured before and after ligand introduction. Any slight ligand-induced variations of sample size will result in large changes of sample conductivity. Swelling will cause the conductivity to drop, and shrinkage will cause it to rise. Another type of technique is to measure changes in ligand-induced thickness or elasticity in the direction of the film's thickness, i.e., changes in the normal direction of the film. The changes in thickness may be measured by ellipsometry or any other optical method. Particularly when measuring normal deformations of the film (i.e., in the direction of thickness), the film is preferably a relatively massive body with intermolecular contacts between protein molecules, as opposed to a molecular monolayer. Even so, the size of the protein sample can be reduced to a micron scale. Changes in elasticity and thickness of the film can also be measured by acoustic methods in which the frequency of a solid resonator is measured. Difference in thickness can also be measured by electrode methods. The impedance of an electrode is sensitive to the thickness of the semiconductive protein film on the electrode, packing protein molecules, their charges and conformation. Changes in electrode impedance can reveal film deformation due to ligand binding. If the protein layer is covered with magnetic particles, their distance from a magnetic sensor may be registered to follow deformation of the film.

Film thickness and normal elasticity can be directly measured using indentors. The depth of indention is a function of the load and the elasticity of the protein or DNA film. A microvariant of the indentor method involves use of an atomic force microscope. The tip of the atomic force microscope may be used as an indentor. Comparison of sample sections obtained under different loads on the tip will allow one to calculate separate deformation and elasticity parameters.

The velocity of traveling acoustic waves through the cross-linked protein or DNA films may be used to measure deformation. These can include Rayleigh waves on the surface of a piezocrystal. The velocity of transmission of transverse or longitudinal waves through the sample strip can be measured directly or by a resonance method in which the length of standing waves in the sample is registered.

The method of the present invention is not limited to the specific techniques discussed above. Any method can be used for measuring a physical characteristic of the sample strip, other than lateral elasticity or lateral tensile properties, which is capable of detecting deformation of the cross-linked structure of the sample strip upon interaction with the ligand. For example, the protein or DNA film may be deposited on the pores of a filter or capillary. Swelling and shrinkage of the film upon ligand interaction can modulate the rate of liquid flow through the capillary, and this parameter can be used to probe the swelling. It is expected that once the present invention is known and understood, those of ordinary skill in the art will be able to devise other acts equivalent to those described in the present specification for performing the steps of the present method claims.

The present invention further relates to methods for forming the sample strip which may be used with the present invention. In one method, strips of a reinforcement material are formed on a surface and the polymeric material to be tested is formed over the surface including at least a portion of the reinforcement strips so as to adhere to the reinforcement strips. The polymeric material and the reinforcement strips adhered thereto are then removed from the surface. The sample strip prepared in this manner is affixed to the tips of the apparatus such that the tips are affixed thereto in the region of the reinforcement strips. In another method, the sample strip is formed by electrospraying the polymeric material on a surface with or without the presence of the reinforcement strips.

When the polymeric material is a protein or DNA material, the protein or DNA molecules are dried after being applied onto the surface and in contact with the reinforcement strips. A film is thus formed on the surface and at least partially overlapping the strips of reinforcement material. The protein or nucleic acid molecules of the film are then cross-linked, followed by removal of the cross-linked protein or nucleic acid material and the underlying reinforcement strips from the surface. The surface of the strips of reinforcement material are preferably pretreated to provide adherence of the film to the reinforcement material. The reinforcement material is preferably gelatin.

BRIEF DESCRIPTION OF THE DRAWINGS

The above and other objects and the nature and advantages of the present invention will become more apparent from the following detailed description of embodiments of the present invention taken in conjunction with the drawings, wherein:

FIG. 2, labeled "prior art", is a perspective view of the apparatus of the prior art;

FIG. 3, labeled "prior art", is a perspective view of the pincers of the prior art;

FIG. 21 schematically shows a method of measuring the deformation of the sample strip by electrical conductivity through the sample strip;

FIGS. 27B–27D schematically represent possible structures of force or deformation sensors. A tunneling current sensor in which deflection of a resilient cantilever is measured by changes in tunneling current between cantilever and a point contact (FIG. 27B). Light reflection or interference induced by the cantilever deflection as shown in FIG. 27C, or changes in the resistance of a conducting layer on the surface of the cantilever as presented in FIG. 27D can also be used as force sensors;

DETAILED DESCRIPTION OF THE PREFERRED EMBODIMENTS

Figures 1, 1A:
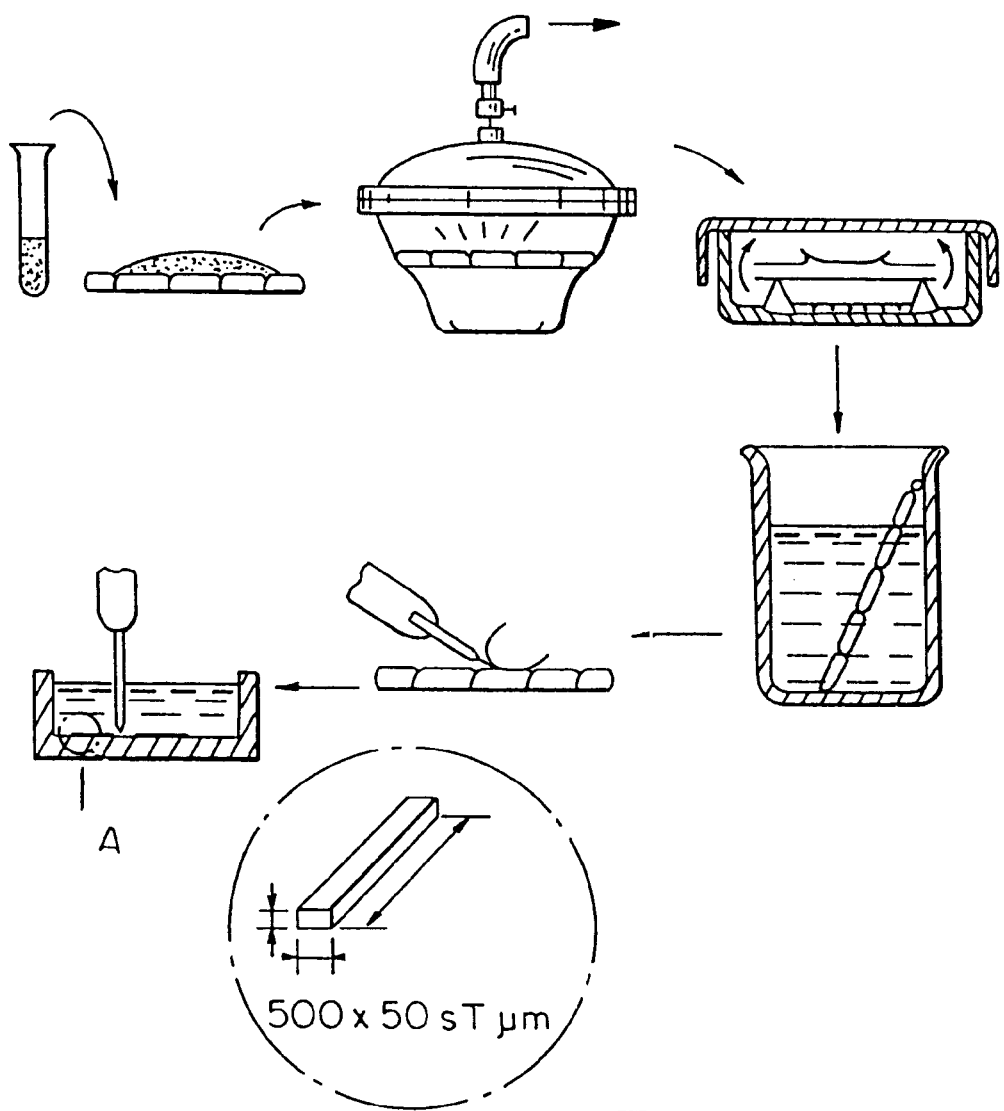
FIG. 1, labeled "prior art", is a schematic view of the prior art process of preparing strips.
FIG. 1A is an enlarged view of area A of FIG. 1.

In its preferred embodiment, the method of the present invention relates to preparing strips of cross-linked material from DNA or protein solutions, the strips being mechanically suitable for stress/strain or mechanical compliance testing, and where the strips include mechanical reinforcement at their ends. The reinforcement, which extends across the width of each strip, makes for simple manipulation of the strip and prevents uneven stretching along different lengthwise extending portions of the strip.

One preferred method of making the strips is to lay plastic reinforcement strips in an evenly-spaced parallel array over a glass surface, wet the surface and strips with a protein or DNA solution, dry the solution, and cross-link the protein or DNA; then cut the reinforcement lengthwise. By this method, each separate sample strip is bordered on either end by one-half of a reinforcement strip.

Another preferred method of making the strips is to deposit protein or DNA by electrospray onto a surface, on which reinforcement strips may be present.

The preferred apparatus, to be used with strips prepared according to the method, has a pair of downwardly-extending supporting members with sample-holding tips at their lowermost extremities. One supporting member is attached to a force transducer and the other to a motion or displacement transducer. The supporting member tips extend downward into a trough or well which holds solution, so that any liquid can be used. The supporting members are held on a vertically-movable transducer housing of the apparatus that rides up and down on precision tracks fixed to a base portion. Alternatively, the transducer can be stationary and the well be movable. The supporting members can be lowered into the well or raised up by the operator's cranking the transducer housing up and down.

A sample holder is preferably used to mount the samples in the apparatus. The sample holder is a jig, including precision locating surfaces for precision mounting of the holder relative to the base. Because both the sample holder and the transducer housing are precisely held relative to the base, the tips of the supporting members can be repeatedly lowered onto the same two points on a sample held in the sample holder, to an accuracy of a few microns, even if the sample holder is removed between lowerings of the transducer housing.

The preferred method of using the apparatus contemplates placing the sample holder onto the base and lowering the transducer housing until the supporting members contact the holder, making marks. The sample strip can then be easily placed over the marks in a position where the supporting member tips will contact it at the correct places. Then the transducer housing is lowered again until the tips make contact with the strip positioned over the marks on top of the sample holder and grasp it. The grasping may be by several methods, including penetration of sharp tip ends through the strip, suction of the sample strip onto the end of capillaries (tips) which have a reduced pressure inside, and adhesive bonding of the strips to the tips; in this latter methods, the tips preferably have flattened ends to provide a suction or glue area.

Figure 19A:
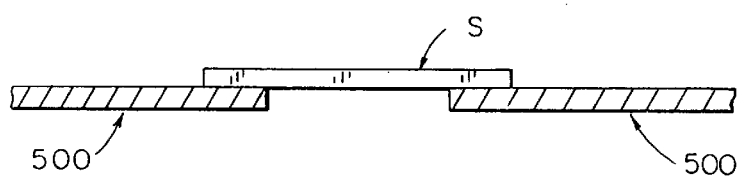
FIGS. 19A–19B schematically show a side view (FIG. 19A) and a top view (FIG. 19B) of the tips of supporting members attached to the sample strip from underneath.
Figure 19B:
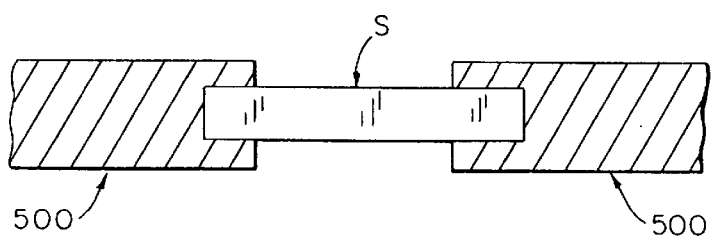

Alternatively, the tips of the supporting members (500) may be glued to the sample strip(s) from underneath as shown in FIGS. 19A and 19B.

Preferably, the strips are penetrated through the reinforcement so that the forces exerted by the tips are spread out by the reinforcement. If adhesive is used, the tips again are preferably adjacent to or on the reinforcement.

After the sample strip is firmly fixed between the supporting members, the transducer housing is raised, the sample holder removed, and the sample strip is lowered into the well and immersed into a reference solution (buffer solution or any other referred as a control, i.e., which is similar to the test solution except for the presence of ligand under analysis or suspected for the presence of such ligand (s)). In this reference solution the strip is stretched by the static strain (displacement) transducer to a fixed length, and then is allowed to relax until constant isometric tension occurs. After the relaxation the reference solution in the flow chamber is changed for the test solution, containing one or more chemical substances tested for their ability to bind protein the strip is made of. Changes in the isometric tension and/or in the elastic modulus is indicative of binding.

In contrast to usual procedure of testing mechanical properties of metals and other materials (where the sample is attached, sensors are activated, measurements are performed etc.), testing protein films consists basically in the detection of changes in the mechanical parameters of protein films when the solution surrounding the film is changed from a reference solution to the one containing ligand(s). The entire procedure is performed with the force sensor on. A single displacement transducer both stretches the sample to a fixed length and varies the length sinusoidally with time by a small amount for compliance testing.

Alternatively, there are two length transducers. A motion transducer, providing oscillatory deformation of the samples, is switched on for certain periods of time while another transducer, providing static deformation, is not active during the testing procedure. The static transducer is used to prepare the sample for testing, for example to stretch it.

The methods of the present invention using the mechanochemical apparatus of the present invention work best when the following elements are adhered to, particularly when the sample member is protein or DNA:

1. The molecules in the sample which are to be tested are cross-linked or are in physical contact.

2. The sample is larger than macromolecules in at least one dimension.

3. At least one dimension of the sample is roughly of the order of a micron. When one dimension is small (thin), the sample is referred to as a film. When two or all three dimensions are small, the sample is referred to, respectively, as a fiber or a bead.

4. The device holds the sample at least one point.

5. The samples are replaceable in the device, either alone or with a holder.

6. The device includes means for changing the composition of a gas or liquid surrounding the sample.

Elements 1 and 2 together distinguish the present technology from other technologies using immobilized proteins. For example, in BIA core devices (Pharmacia), proteins are immobilized on a gold surface but never bind to one another.

The distinction between a force sensor and a deformation or displacement sensor is that a force sensor has a compliance which is much less than that of the sample, while a displacement sensor has a compliance which is much greater than that of the sample. The same holds true for transducers. Transducers and/or sensors are means for setting and/or measuring force and means for setting and/or measuring displacement; the same device may be used for setting or fixing, and also for measuring. In the present invention, any type of force sensor (transducer), and any type of deformation sensor (transducer), can be used.

The invention contemplates dynamic measurement of strain at a fixed stress and also dynamic measurement of stress at a fixed strain. Unlike in the prior-art method, the invention also may hold the force constant and measure the strain. That is, the sample is held at a fixed stress or force F and the strain is allowed to vary. First the sample will relax; then the force may be oscillated and the resulting elongation measured. One apparatus can be used for both of these modes of measurement.

It is to be noted that the apparatus of the present invention preferably stretches the sample strip prior to testing. There are two reasons for this: one is that the test is more sensitive when the strip is stretched; the other is that the stress-strain relation is upset if the strain or elongation of the strip drops below zero: it buckles and ceases to act according to Hooke's law, or even in approximation to it (unless the strip is made very thick or very short, either of which will greatly decrease or destroy the sensitivity of the test). Once the strip is under zero tension, spring constant measurements are impossible.

In the preferred embodiment of the present invention, the displacement transducer constitutes a means for stretching.

It is also to be noted that the present invention uses a measurement of elasticity—a relation between force and length—to determine binding in the sample strip. The present invention does not necessarily measure any dimension of the sample strip; indeed, in the preferred mode of the invention the strip length is held constant or varied slightly according to a predetermined pattern: it is an independent variable. The dependent or measured variable is force.

In an alternate mode of measurement of the present invention, the elasticity is also measured while the strip is stretched using the same two quantities, but the deformation or displacement is the measured quantity while the force is predetermined. Even in this alternate mode, the measured quantity, dimension, does not provide a direct measure of ligand binding; only the ratio of dimension and force provides the end result.

The force means for applying force to the strip may include a spring as well as or in addition to an active transducer/sensor. If one end of the strip is attached to such a spring, then the displacement of the sprung end will be proportional to the stretching force, and this displacement can be measured by a suitable sensor.

Figure 20A:
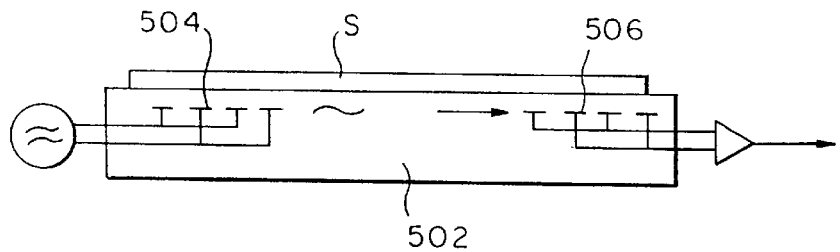
FIGS. 20A–20D schematically illustrate wave-type methods for measuring deformation and changes in elasticity from the velocity of traveling acoustic waves.
Figure 20B:
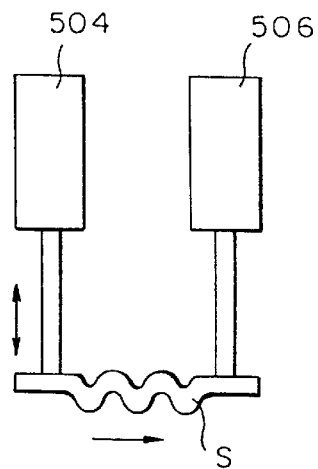
Figure 20C:
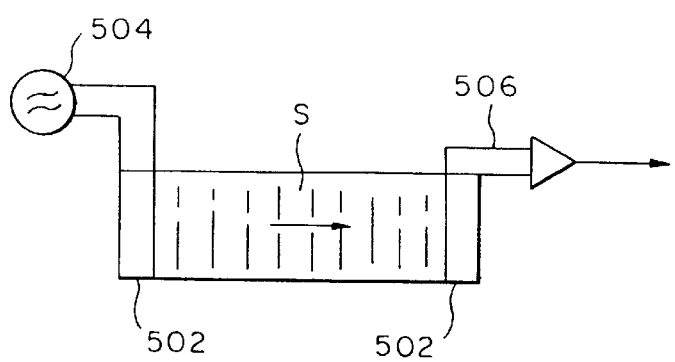
Figure 20D:
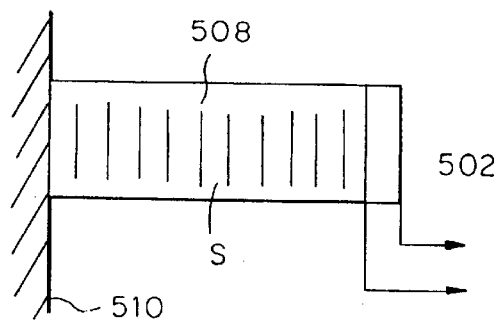

While various transducers are disclosed as specific embodiments of the means for applying force to the sample strip, it should be understood that any such means for applying force may be used to apply force to the sample strip held by the tips of the apparatus. Once force is applied, for example, by stretching the strip or at least maintaining the strip in a fully extended and non-buckled position, other actions may be applied to the strip in order to measure other characteristics of the strip, which will result in a quantitative measurement of the effect of chemicals on the strip. Thus, for example, electrical energy or acoustic energy may be applied to the strip. Similarly, the measurement means may measure not only elasticity but also chemical, mechanical or electrical properties, depending on the action which is applied to the sample. Thus, the manner in which an electrical signal or acoustical wave passes through the sample, before and after being subjected to the chemical, may be measured. For example, changes in the velocity of travelling acoustic waves through the film may be used to probe ligand binding by measuring deformation and changes in elasticity of the film (FIGS. 20A–D). These wavelength methods for measuring deformation and changes in elasticity can include ligand-induced changes in mass and elasticity of the sample strip(s), e.g., protein film, on the surface of a piezocrystal (502) (FIG. 20A) which can be registered by variation of velocity of Rayleigh waves generated by a wave generator (504) and measured by a wave sensor (506). The velocity of transmission of transverse (FIG. 20B) and longitudinal (FIG. 20C) waves through the sample strip can be exploited to probe ligand binding and be measured directly or by a resonance method in which the length of standing waves in the sample is registered (FIG. 20D).

Phase, impulse and resonance methods known in the art can be used to measure velocity of wave propagation in all these wave-type structure methods. A wave generator 504 and a wave sensor 506 for measuring velocity of wave propagation in sample strip S are shown in FIGS. 20B and 20C. In FIG. 20C, piezocrystals 502 are connected to sample strip S at both ends, whereas in FIG. 20D, a piezocrystal 502 is only positioned at one end of sample strip S to measure standing waves 508, and the other end of sample strip S is attached to a rigid wall 510.

Another example, shown in FIG. 21, involves the inclusion of conductive particles 514, such as carbon powder, in the polymeric material of the sample strip to be tested. The conductivity through the sample strip S is measured between electrodes 512, where slight ligand-induced variations of sample size (e.g., swelling), as shown in the lower part of FIG. 21, will result in large changes in sample conductivity as the contact between conductive particles are lost. This is the simplest protein sensor as only a means for measuring sample conductivity between the electrodes is needed. In one embodiment, the tips of the apparatus according to the present invention may be used as the electrodes.

Figure 22A:
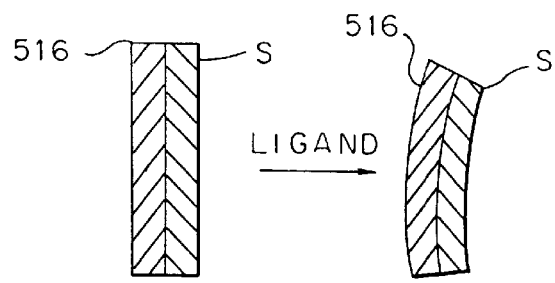
FIGS. 22A–22C schematically show bimorph structures and examples of measuring the bending of the bimorph due to ligand-induced deformation.
Figure 22B:
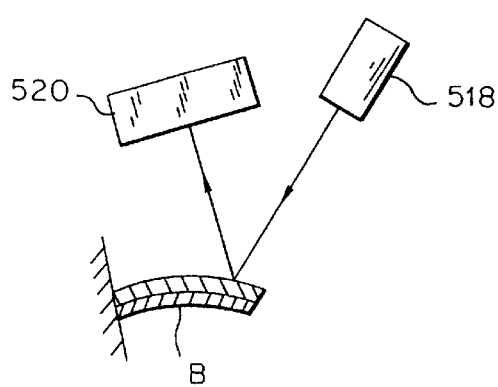
Figure 22C:
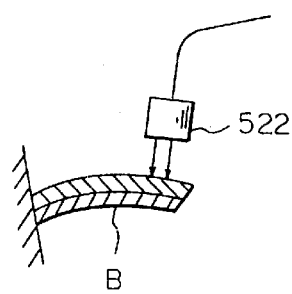
Figure 23:
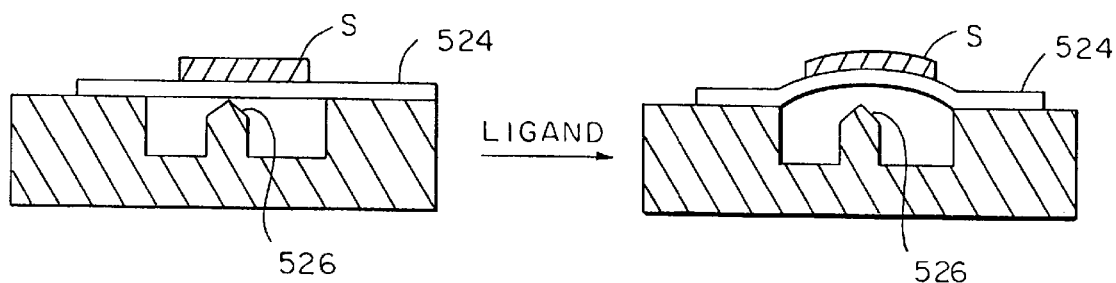
FIG. 23 schematically shows ligand-induced changes in a strain sensitive structure as measured by a tensoresistive sensor.

A further example is a bimorph structure (FIG. 22A) which consists of two layers, one of which is a sample strip layer S and the other layer 516 can be made of a material which is not affected by ligand, a strain- or stress-sensitive material (e.g., piezoelectric), or the same cross-linked protein or DNA in which the ability to bind ligand is blocked by modification. Upon exposure to a ligand solution, such a bimorph bends due to deformation of the sample strip layer S. In FIG. 22A, the shrinkage of sample strip layer S causes bending of the bimorph structure, and bimorph bending can be measured by any suitable method, i.e., optical, electrical, etc., with the advantage of simplicity and a differential response. FIGS. 22B and 22C show that deformation of the bimorph structure B can be detected optically by a light source 518 and a position-sensitive light detector 520 (FIG. 22B), and by a distance sensor 522 (FIG. 22C). The ligand-induced changes in strain (stress) on a strain sensitive structure, such as a modified bimorph in which a sample strip S is deposited on a strain sensitive surface 524 (FIG. 23), can also generate an electrical signal to a sensor 526 in a manner similar to known tensoresistive sensors. Sample preparation of such a modified bimorph is simple, and amenable to mass fabrication.

Figure 24:
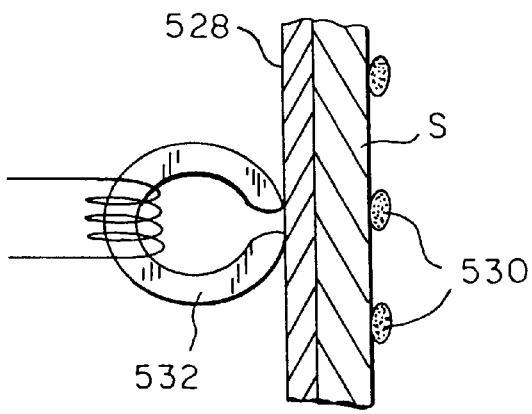
FIG. 24 schematically shows a magnetic method for measuring ligand-induced changes in film thickness.
Figure 25:
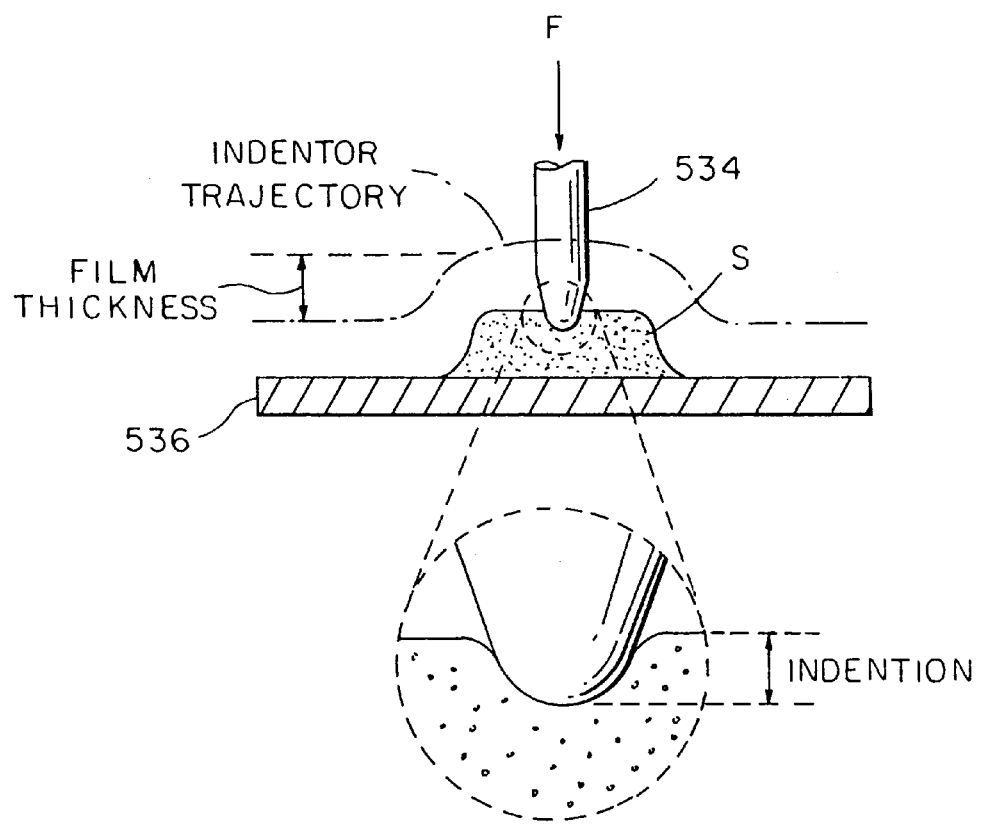
FIG. 25 schematically shows the indentor method for directly measuring ligand-induced changes in film thickness and elasticity.

When the sample is deposited as a film on a support, then ligand-induced changes in film thickness and/or rigidity can be measured by: (1) ellipsometry or other interferometric optical methods where swelling/shrinking results in changes in both thickness and refractive index of the layer; (2) acoustic methods in which changes in the resonance frequency of a solid resonator, such as a quartz crystal, are measured in response to changes of film thickness and elasticity upon film deformation (e.g., swelling); (3) electrode impedance methods where the sample film is deposited on a conducting surface and impedance changes of such electrode, which may result from changes in effective dielectric constant due to film swelling, changes in concentration of counterions upon binding of charged ligands, changes in ionic conductivity of the sample film, etc., can be used to detect film swelling upon ligand binding; (4) magnetic method (FIG. 24), in which the sample film layer S deposited on a foil layer 528 is covered with magnetic particles 530, and which measures the deformation of the film thickness, upon ligand binding, by determining the distance of the magnetic particles 530 from a magnetic head 532; and (5) indentor method, as shown in FIG. 25, where film thickness and rigidity are measured directly by an indentor tip 534, such as a tip of an atomic force microscope, as it moves from a position over the substrate 536 to a position over the sample film S, where the depth of indention is a function of load and elasticity of the sample film. Measuring film thickness under different forces F as applied by the indentor tip in the indentor method allows for determination of film elasticity. The larger the compliance of the film, the more the film is deformed under the indentor tip and the smaller the measured film thickness. The indentor method offers the advantage that simultaneous detection with different samples can be achieved, leading to high throughput screening of samples. All of these processes which involve measurement of normal deformation (as opposed to the lateral measurements of the prior art) have the advantage of permitting reduction of the size of the protein or DNA sample to a micron scale, although preferably thicker than a monolayer.

Figure 26:
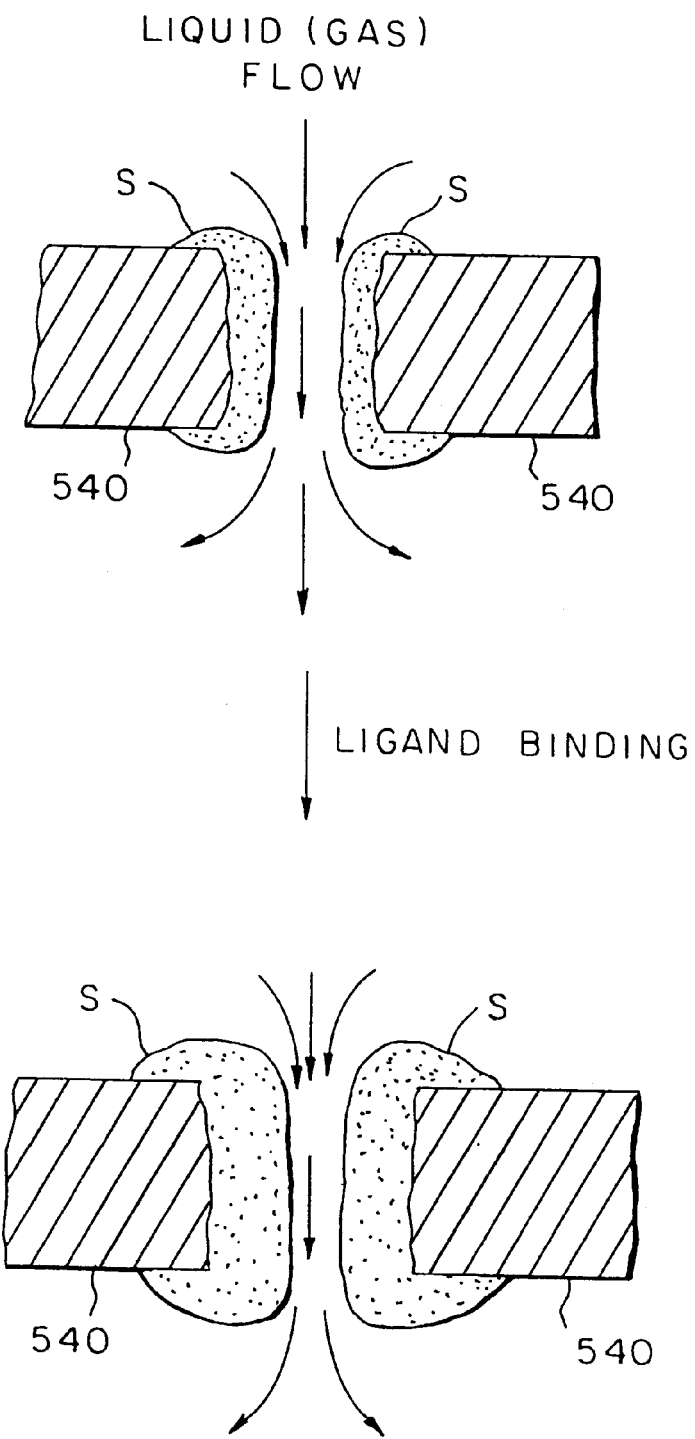
FIG. 26 schematically shows a method where deformation of protein film in a flow channel can modulate the rate of liquid flow through the channel.

In yet another method, as shown in FIG. 26, the deformation of the sample film S upon ligand binding can be measured as a function of fluid flow through a channel, i.e., capillary, pores in a filter, etc. The deformation (swelling or shrinkage) of sample film S, deposited on the channel walls 540, in response to ligand modulates the flow rate of a liquid or gas through the channel(s), and this flow rate parameter can be used to probe sample film deformation.

Figure 28A:
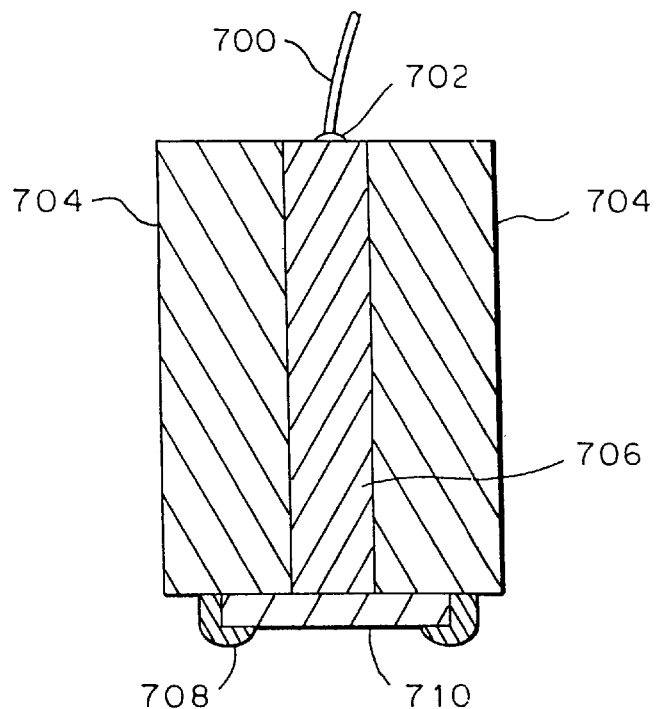
FIGS. 28A and 28B schematically show a method for measuring electrical conductance of the sample film.
Figure 28B:
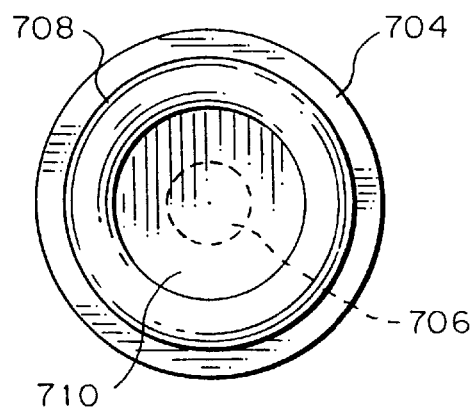
Figure 29:
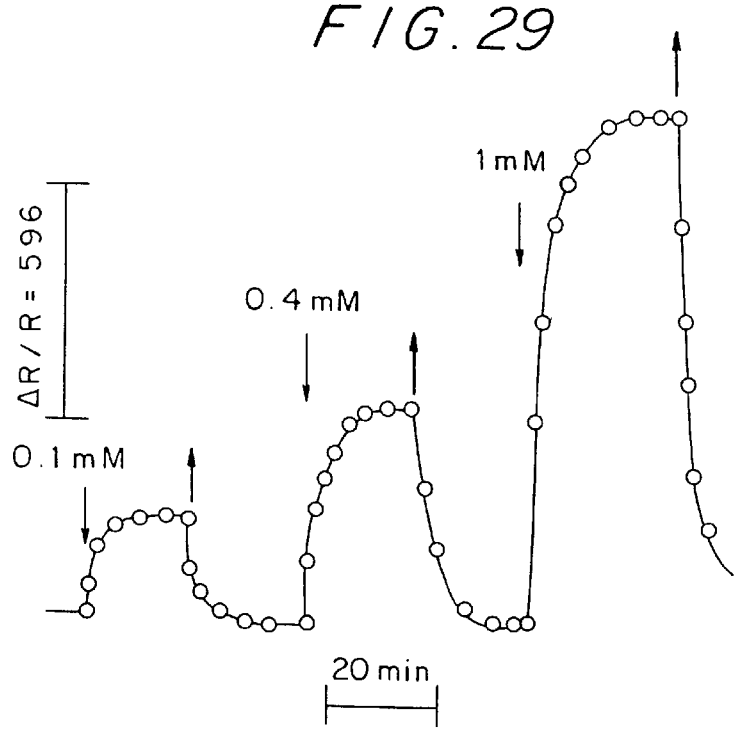
FIG. 29 shows the ligand-induced change in resistance of a hen egg white lysozyme film prepared from triclinic lysozyme crystals. Downward arrows indicate time points where a 2,5-dinitrophenyl solution in the concentrations shown were added. Upward arrows indicate time points when a washing solution containing 0.1 M NaCl, pH 4.6, was added.
Figure 30:
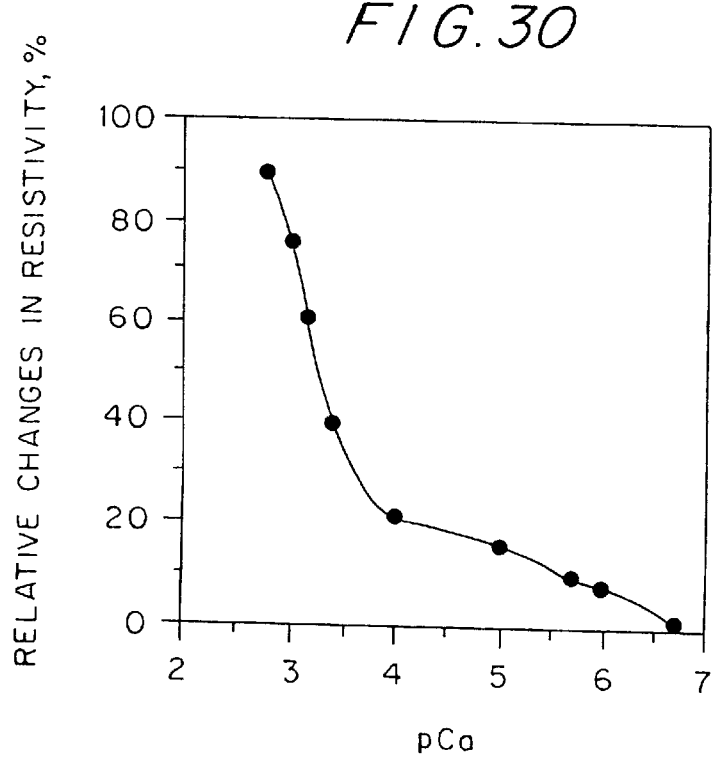
FIG. 30 shows the changes in resistance of an amorphous cod parvalbumin film in response to binding of Calcium ions. Measurements were performed in 1 mM Ca-EDTA buffer, pH 6.0, 0.1 M NaCl.

FIGS. 28A and 28B show a cross-sectional view and a plan view, respectively, of a method for detecting deformation of a sample film upon interaction with a ligand by measuring the change in the electrical conductance of a sample film 710. The sample film 710 is glued to the end of an electrode and in contact with a wire 706, e.g., platinum wire, surrounded by an insulator 704. A conductor 700 is connected to the wire by a spot of solder 702. The edge of the protein film is covered with a layer of insulating glue to prevent current leakage when the sample film is immersed in a solution, such as a ligand-containing solution, to complete the circuit for measuring electrical conductivity through the sample film.

Figure 27A:
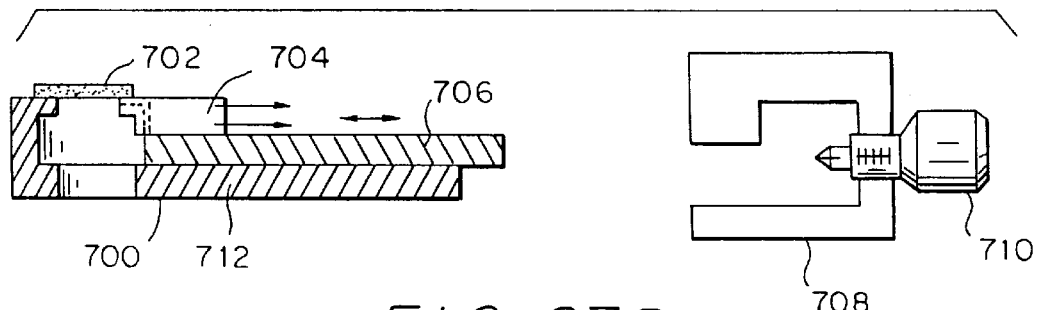
FIGS. 27A–27D schematically illustrate a chip-type structure of a mechanochemical testing device in which a sample film, a sample holder and force transducer are combined into a compact unit (FIG. 27A) which is detachable and disposable.

A force transducer, force sensor and sample film (e.g., protein) can be combined in a single unit as schematically illustrated in FIG. 27A, where one advantage is the easy replacement of such an integrated unit, which can even be used as a disposable unit. In FIG. 27A, a detachable chip 700 is composed of a replaceable combination of a sample film 702, a force transducer 704 (force sensor) and a means to induce film deformation 706, which means is a movable part. The detachable chip 700 is placed in a measuring unit 708 which has a means 710 to move the movable part 706. Film deformation is performed by shifting the movable part 706 relative to the base 712.

Figure 27B:
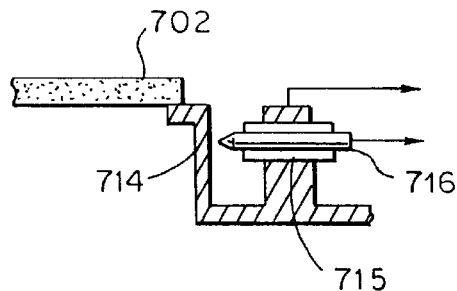

One type of force sensor used in the detachable ship 700 shown in FIG. 27A is illustrated in FIG. 27B. In this sensor, changes in tunneling current are used to measure the deformation of a resilient cantilever 714 attached to the sample film 702 under applied force. Tunneling is a process of electron transport through a small gap (approximately 0.1–2 nm) between one electrode 716 with insulator 715 and a second electrode, which is also the cantilever 714, where the tunneling current is highly dependent on the gap, and its value is used to measure force as a deformation of a calibrated spring (cantilever).

Figure 27C:
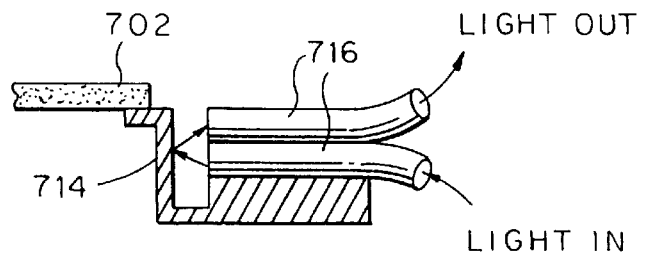
Figure 27D:
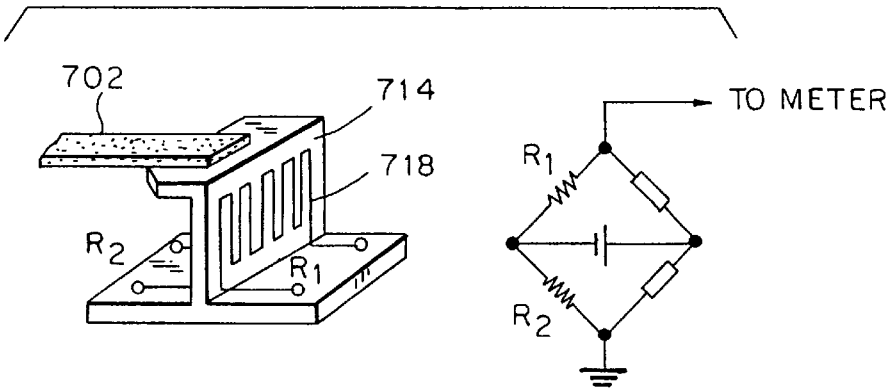

Another type of force transducer for a detachable mechanochemical chip measures cantilever 714 deflection by detecting changes in the intensity or direction of reflected light at a light detector, such as by using optic fibers 716 (FIG. 27C). FIG. 27D illustrates a further type of force transducer in which both sides of the cantilever are covered with a deformation-sensitive coating, such as a tensoresistor 718, and changes in creating conductivity in response to cantilever bending are used to measure force.

Also within the scope of the present invention are various attachments of the samples to the device, in addition to gluing and pinning. For example, hot-melt adhesive (thermoglue) could be used, made of a material which solidifies at a relatively low temperature. Or, samples could be attached using a magnetic liquid that solidifies in a magnetic field (magnetic glue). Still another alternative is the use of atmospheric pressure to attach the sample to the ends of capillary tubes under suction.

The following detailed description first describes the apparatus used for the test of the invention, then describes the preparation of samples (strips of protein or DNA material), next describes the test procedures (using the apparatus to measure changes in the mechanical properties of the sample strips as a result of their immersion in a ligand-containing solution), and finally discusses the results of the invention.

Figure 4:
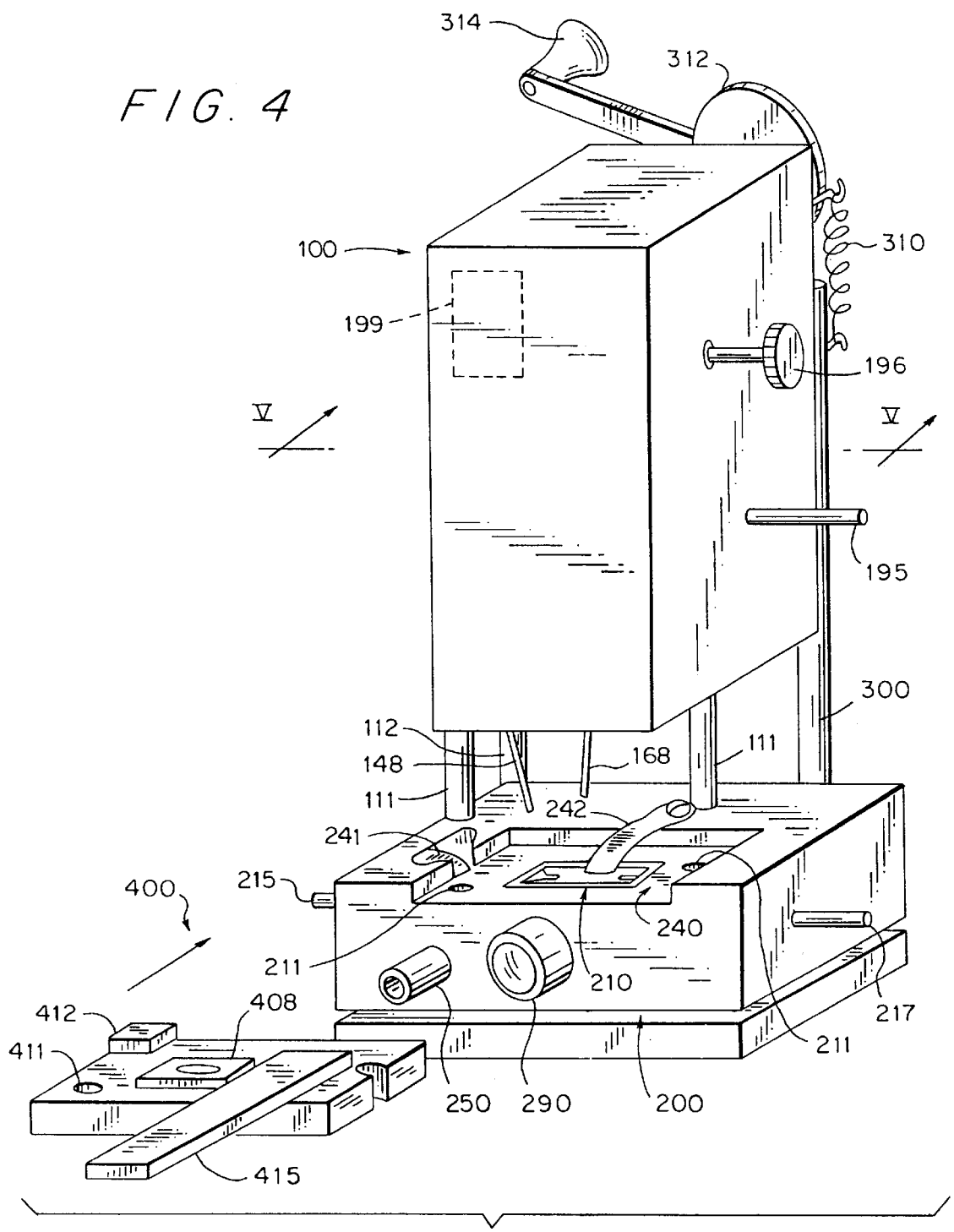
FIG. 4 is a perspective view of an apparatus of the present invention.

The invention is shown in overview in FIG. 4. It includes a base 200 which slides up and down relative to a transducer housing 100 on a vertical track 300. Alternatively, the housing 100 may slide. A sample holder 400 can be mounted on the base above a solution well 210.

Figure 6:
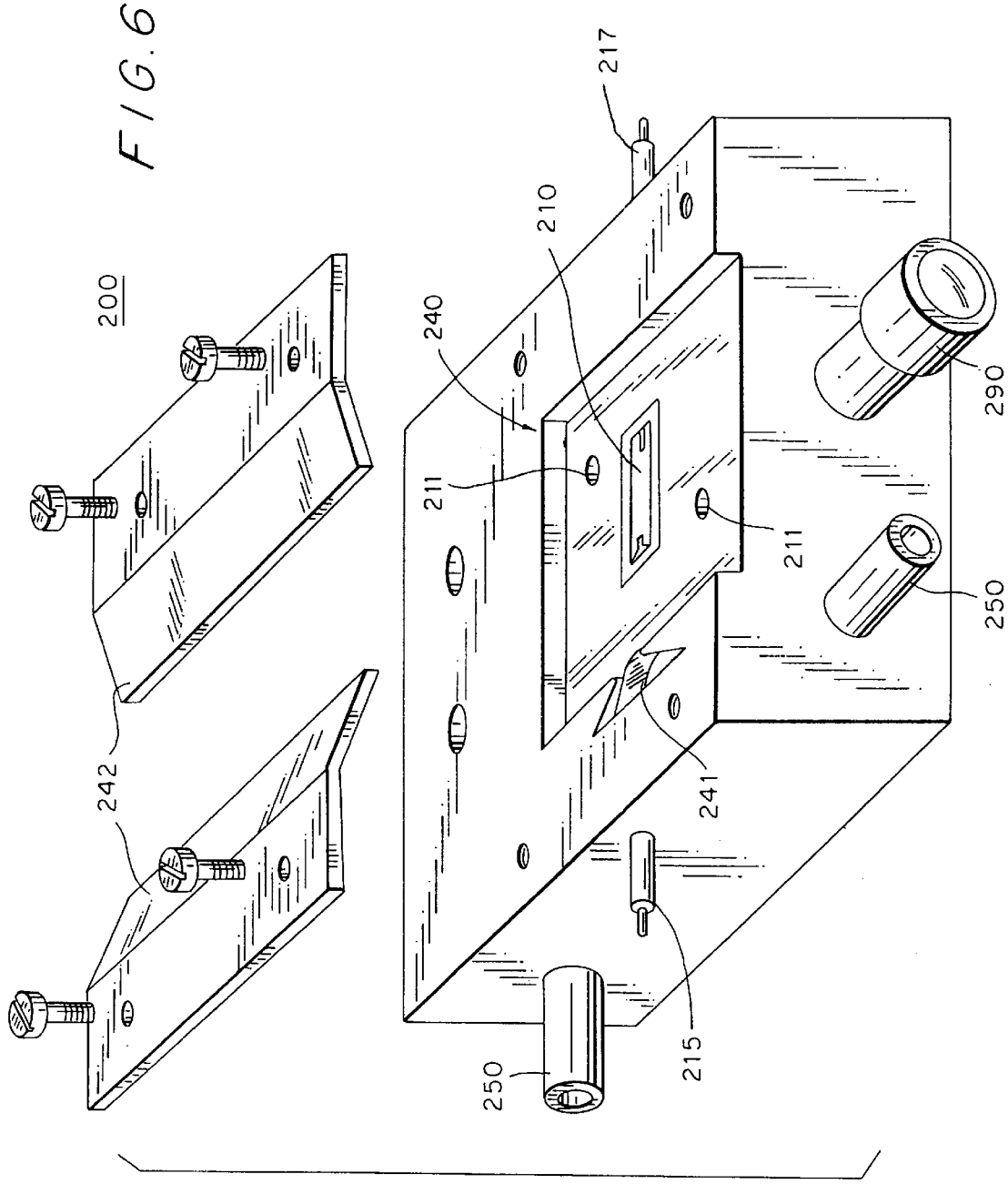
FIG. 6 is a perspective view of the base.
Figure 7:
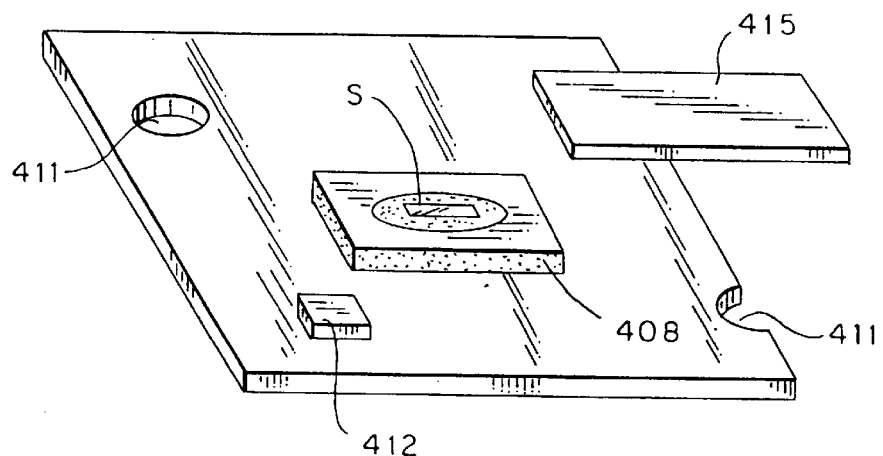
FIG. 7 is a perspective view of the holder.

The sample holder 400 includes a handle 415 for sliding the holder 400 into and out of a recess 240 in the top of the base 200. The recess 240 is sized to accept the holder 400 closely, but not tightly. The holder should repeatably assume a fixed position relative to the base 200 even while being removed and replaced into the recess 240. When the holder 400 is inserted into the recess 240, springs 241 and 242 urge the holder 400 downward and to the right as viewed in FIG. 4, taking up any slack. (FIG. 6 shows an alternative embodiment of the hold-down spring 242.) Because of this, the holder 400 assumes exactly the same position each time it is inserted into the recess 240, with a precision of several microns. Such precision is achievable by conventional jigging techniques. Any conventional jigging arrangement other than that illustrated may be used to precisely and repeatably locate the holder 400 in the recess 240.

A sample support pad 408 is preferably adhered to the top surface of the holder 400.

Figure 5:
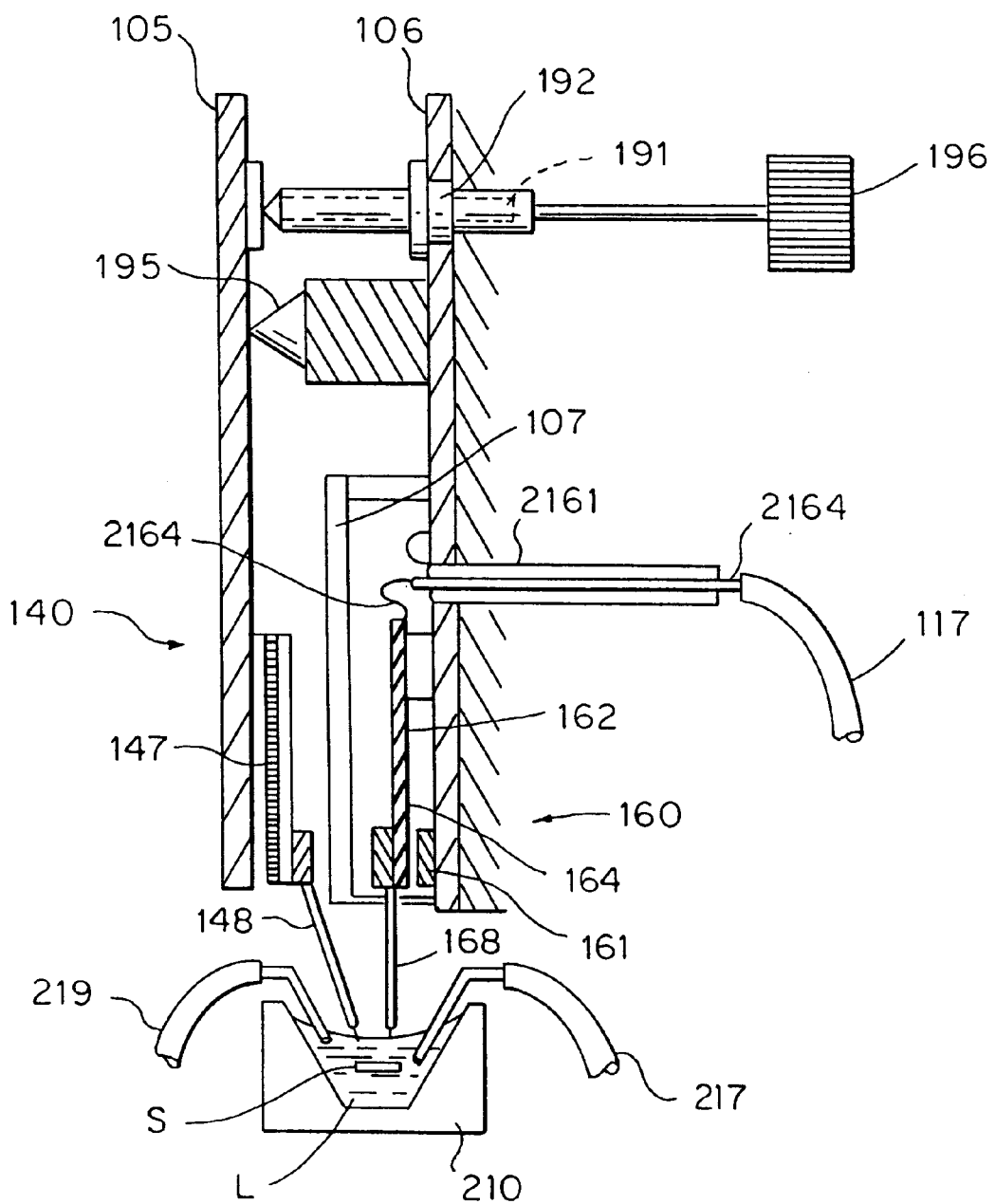
FIG. 5 is a partial cross-sectional view taken along lines V—V of FIG. 4.

FIGS. 4 and 5 show the transducer housing 100, which is analogous in function to the prior art device of FIG. 2. From the lowermost part of the transducer housing 100, supporting members 148 and 168, which may be more appropriately referred to as arms in FIGS. 4 and 5, protrude toward a sample space defined in the base 200. The sample space includes a portion of the recess 240 and also a solution well 210 which is located directly below. The arms 148, 168 can be moved into the well 210 for sample testing.

The transducer housing 100 (or the base 200) is vertically movable along a track 300, which is preferably a precision, optical-grade track. The transducer housing 100 is sprung upward by a spring 310, which takes up slack against a rotatable eccentric cam 312. When the cam 312 is turned by a handle 314 the transducer housing is moved upward and downward, and the tips of the arms 148, 168 can be lowered onto the sample holder or into the well 210. Alternatively, an automatic mechanism for raising and lowering the housing 100 may be provided, which may include position sensors and computer-controlled servomechanisms.

The downward travel of the housing 100 is limited by fingers 111 and 112 that extend from the lower part of the housing 100. When the housing 100 is fully lowered, the longer fingers 111 insert into holes 211; the housing is stopped when the fingers 111 bottom out in the holes 211. When the holder 400 is in the recess 240, the fingers 111 pass through aligned holes 411 in the holder. However, the fingers 111 cannot bottom out when the holder 400 is in that position because the shorter finger 112 butts against a stop plate 412 on the sample holder 400. Thus, the housing 100 may be raised so far that the fingers 111, 112 clear the recess 240 and allow the sample holder 400 to be emplaced; lowered to a fixed intermediate position when the holder 400 is in position; or drop down to a lowermost position when the holder 400 is removed from the recess 240. The intermediate position is for emplacing the tips of the arms 148, 168 on a sample, and the lowermost position is for testing the sample while it is held within the well 210.

The fingers 111 and the holes 211 may act as jig elements to replace or augment other jig arrangements for precisely locating the holder 400 in the recess 240. That is, when the holder 400 may be held against the fingers 111 by the springs 241, 242. The fingers 111 have the advantage of being fixed to the housing 100, so that they are more precisely located to the arms 148, 168 than is any part of the base 200. The base 200 moves, relative to the housing 100, by a distance equal to the play in the track 300.

Figure 8:
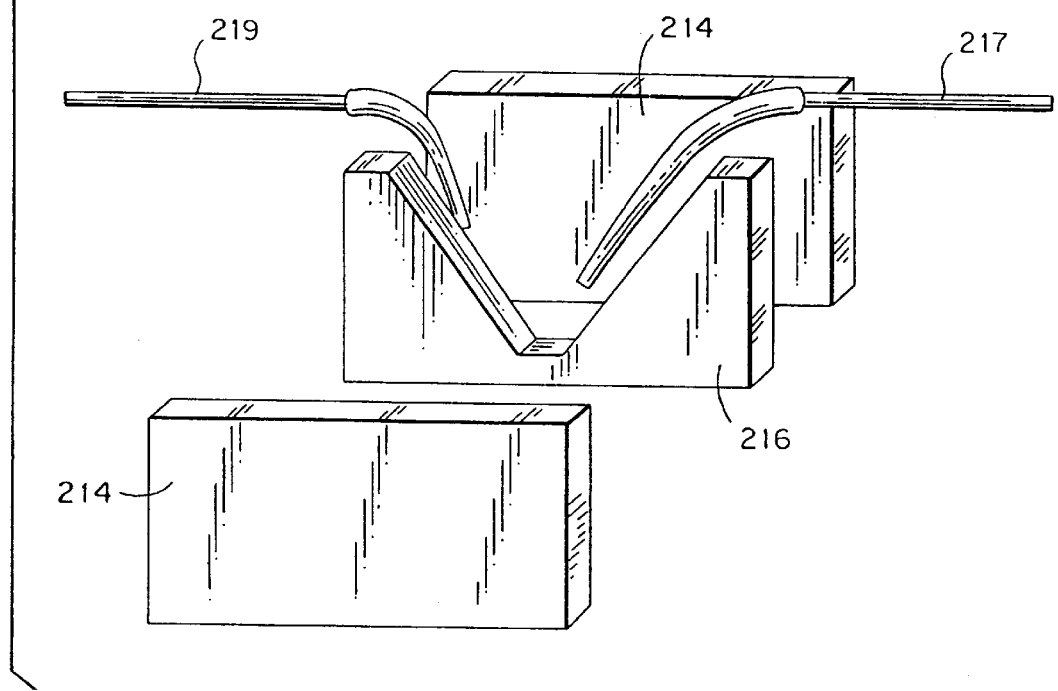
FIG. 8 shows cross-sectional views of the flow cell.

The well (or, flow cell) 210 is shown in FIG. 8, removed from the base 200. An inlet tube 217, on the right in FIG. 8, injects solution into the well. Tube 219, at a higher elevation, removes excess solution. The interior surface of the well is preferably hydrophobic. The well 210 may be constructed from a middle plate 216 and two end plates 214 as shown. It may also be formed in other ways, for example by injection molding or milling of a solid block. It is preferably made of transparent or translucent material. As seen in FIGS. 4 and 6, the well 210 may be illuminated from below through an optical system built into the base 200, including a magnifying or converging lens 290. The lens 290 may be adjustable for different external light sources (not shown).

The base 200 may include internal conduits and external connections 250 for circulating fluids through the base, for the purpose of maintaining the base 200 and thus the well 210 at a constant temperature.

FIG. 5 is a cross section showing the part of the transducer housing 100 including the transducers, and also the well 210. Arms 148, 168 hold a strip S in solution liquid L. As in FIG. 2, the arms 148, 168 extend from respective transducers.

A displacement transducer 140 includes an element, preferably a quartz piezo-electric bimorph, which bends in response to electric voltage. The transducer 140 is mounted on a plate 105, preferably made of quartz for dimensional stability, that is adjustable to allow for moving the tip of the arm 148 left and right as shown in FIG. 5. The plate 105 hinges around a pivot 195 (preferably the apex of a quartz prism), which is fixed on the inside of the plate 106. The plate 105 is rotatable about the pivot 195 by a threaded shaft 191 engaging a threaded hole or fitting 192 in a second quartz plate 106, which is also fixed to the housing 100. By turning the knob 196 on the shaft 191, the arm 148 is moved to and fro.

A force transducer 160 includes a resilient member 162, preferably of quartz, coated with a metal layer 164 which is connected to a lead 2164. An adjacent metal layer 161 adjacent and parallel to the layer 164 forms a capacitor, whose capacitance varies with the distance between the two layers 161, 164, which in turn varies with the force exerted on the tip of the arm 168, which force moves the resilient member 162. The metal layers 161, 164 are preferably of gold to avoid corrosion.

The capacitance force transducer can be replaced by any other comparable (in terms of force scale, precision, and stability) to the preferred transducer. Any other type of transducer, based on any other physical mechanism, can be used in the device as an alternative to the capacitance-transducer, provided it satisfies above-mentioned conditions.

To reduce stray electric fields around the transducers, all internal parts are coated with metal film, preferably silver, to form a Faraday shield. An additional shielding box 107 surrounds the force transducer 160, which is sensitive to moisture. The layer 164 may be grounded to be at the same potential as the metallic lining of the plates. The housing 100 is preferably also metallic to provide additional field isolation. With proper shielding, the electronic circuitry 199 (FIG. 4) connected to the transducers may also be mounted in the housing 100. The leads 2161 and 2164 are coupled to the circuitry 199.

When the circuitry is mounted within the housing 100, the housing 100 is a complete measurement unit, which may be coupled to display devices, computers, and the like to augment its functions. The invention also includes a measurement unit that includes only transducers, and places all the electronics elsewhere.

Moisture as well as stray electric fields can affect capacitance, so dry clean air is piped into the box 107. The lead 2164 preferably along a part of its length comprises a metallic pipe used for blowing the air in.

The preferred quartz construction helps to eliminate errors due to changes in the dimensions of the mechanical elements (quartz has a very low temperature expansion coefficient).

The stiffer the member 162, the less the distance changes between the gold layers 161, 164, and the less the capacitance changes, and the more accurate must be the transducer. Preferably, the resilient member 162 of the force transducer 160 is stiff, so that when a sample strip is stretched between the arms 148, 168, the arm 168 moves only a little; if the arm 168 movement is much less than the stretch of the sample strip, then no correction needs to be made for the displacement of the member 162.

An alternative construction is to combine the resilient arm 162 and the bimorph into a single element, using one metal layer on the resilient member both as an element of the capacitor and an element of the bimorph; in this construction, only one arm is movable and the other arm is fixed to the housing 100. Such a construction allows easy calibration of the motion of the resilient member under force.

Figure 18:
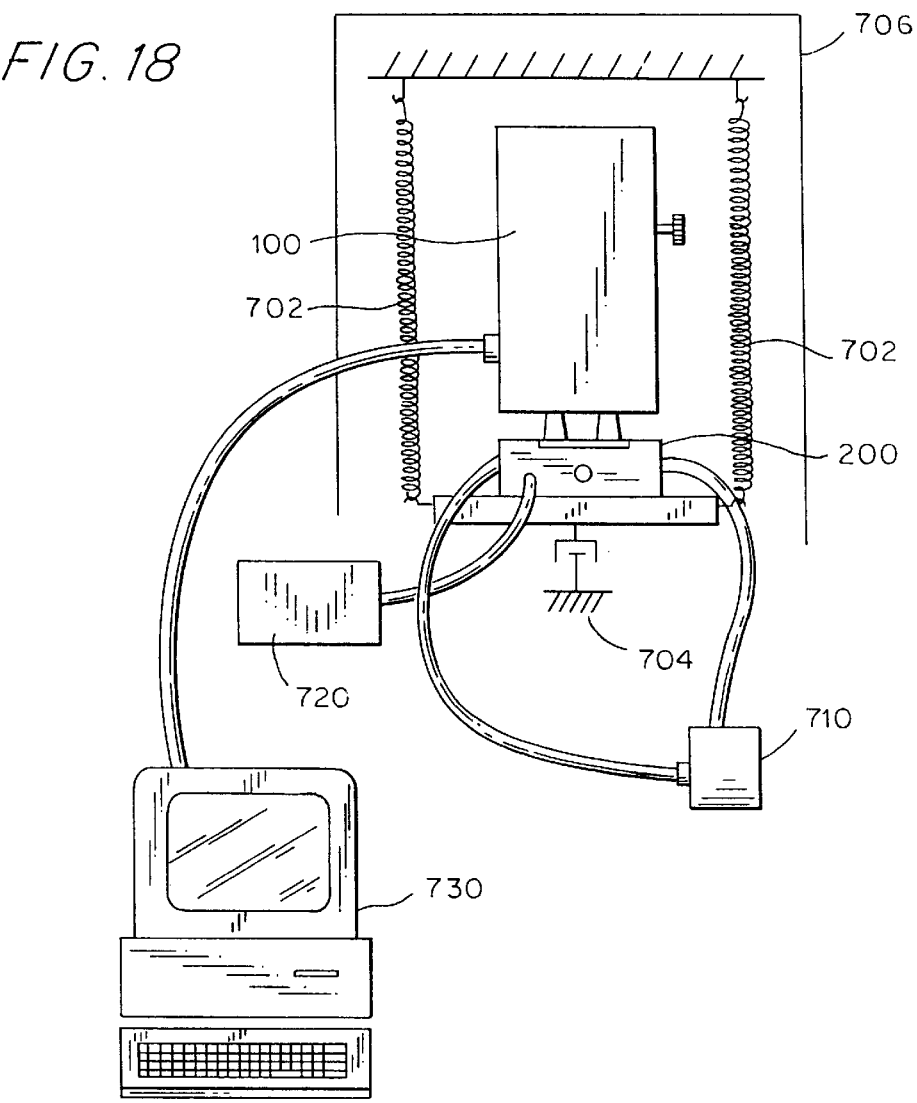
FIG. 18 is a schematic view of the measuring device.

FIG. 18 shows the measurement unit or housing 100 mounted on springs 702 and damped by a dashpot 704. Preferably, there are three layers of springs vibration isolation. Any suitable dampers, such as eddy-effects magnetic dampers, may be used. A shield 706 may be used for thermal, electromagnetic, or other kinds of shielding. A pumping system 710 for ligand and buffer solutions may optionally be part of the invention, as may an isothermal system 720. The transducers 140, 160 and/or any electronics in the housing 100 may be coupled to a computer 730.

FIGS. 9A–9D, in combination with FIG. 4, show one method of mounting a sample strip S onto the arms 148, 168.

Figure 9A:
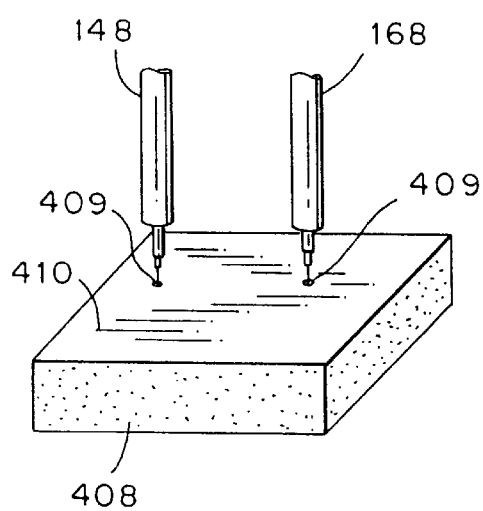
FIGS. 9A–9D are schematic perspective views of the tips and holder, showing a process of attaching the tips to a strip.

In FIG. 9A shows the position of the support pad 408, which is mounted on the upper surface of the sample holder 400, after sample holder 400 has been placed in the recess 240 (see FIG. 4). The sample support pad 408 is preferably made of relatively soft material such as foamed plastic (e.g., Styrofoam) and is covered with a material 410 such as aluminum foil that is easily dented, and on which indentations are easily seen.

The sharp tips of the arms 148, 168 are lowered onto the foil by operating the handle 314 until the finger 112 stops against the stop plate 412 (see FIG. 4); at this intermediate position of the housing 100, the tips just prick the material 410, leaving indentation marks (shown representationally by circles 409).

Figure 9B:
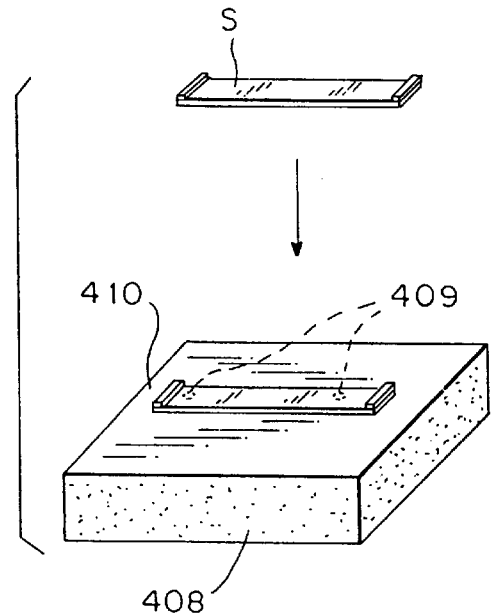

The housing is then raised and the holder 400 is removed from the recess 240. As seen in FIG. 9B, a sample strip S is then lowered onto the support pad 408 in a position where the strip S covers the two pricks 409.

Figure 9D:
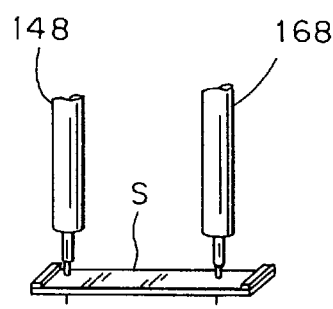
Figure 9C:
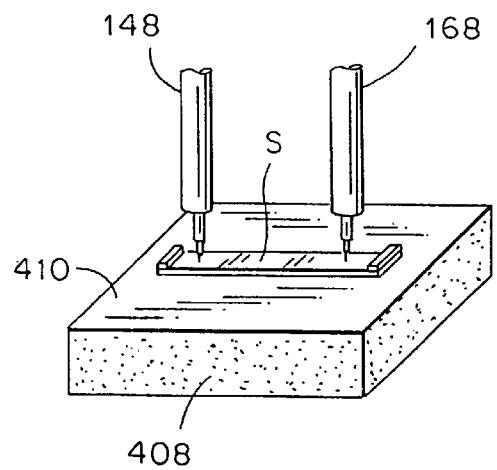

FIG. 9C shows the tips being lowered onto the sample strip S after the holder 400 has been replaced in the recess 240 (FIG. 4). The sharp tips penetrate the strip S.

In FIG. 9D, the housing 100 has again been raised. The sample strip S, now impaled upon the arms 148, 168, is removed from the support pad 408 and holder 400. The strip is now ready to be lowered into the well 210 for mechanochemical testing in solution.

Figure 10A:
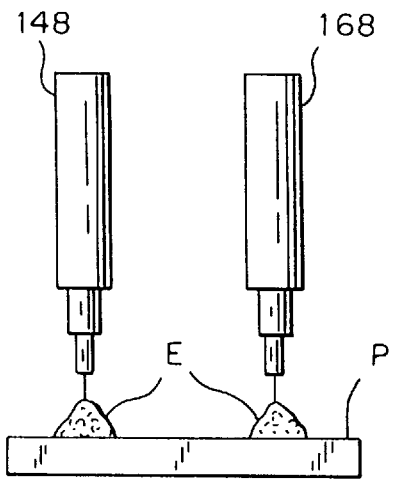
FIGS. 10A–10D are schematic cross-sectional views showing an alternative process of attaching the tips to a strip.
Figure 10B:
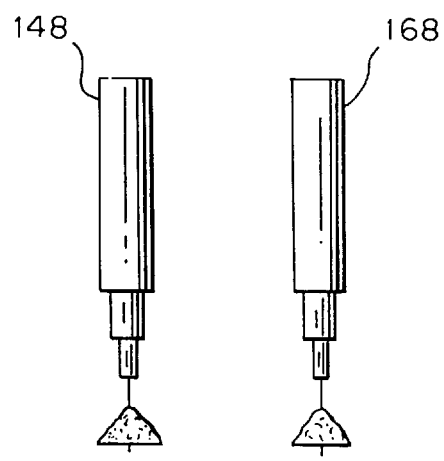
Figure 10C:
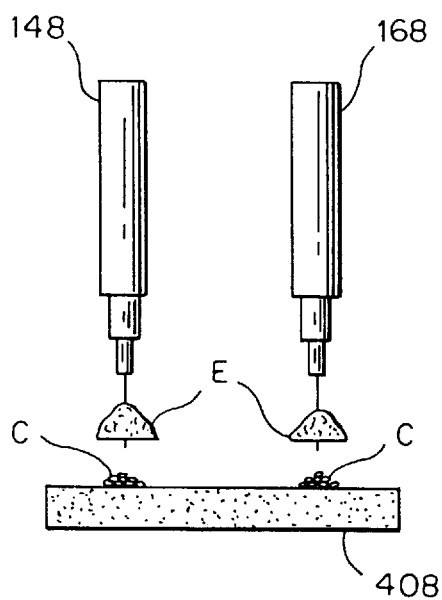
Figure 10D:
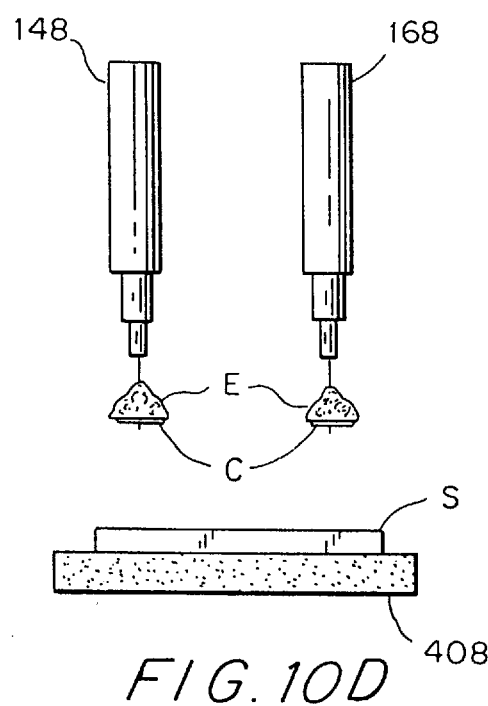

FIGS. 10A–10D show an alternative sample strip attachment that is preferred for soft sample strips which cannot be pinned (as in FIGS. 9A–9D). In FIG. 10A the tips are lowered onto a sheet or plate P of plastic, far enough to very slightly penetrate the plate P. Micro-droplets E of a polymer such as epoxy are placed on each tip and allowed to harden. The plate P is of a suitable material, such as Teflon, which does not adhere to epoxy or other resin; this allows the plate P to be removed, as in FIG. 10B. The tips protrude slightly, as seen in the drawing; this allows the tips to be brought down onto the support pad 408 to make prick-marks. An adhesive such as cyanoacrylate (e.g., Loctite) is then placed onto each prick-mark as shown in FIG. 10C, and the tips are quickly lowered and then raised, becoming wetted with but not adhered to cyanoacrylate due to the short compression time. Finally, as seen in FIG. 10D, the sample S in emplaced over the prick-marks as described above in relation to FIG. 9. When the tips are lowered onto the sample strip S and held for several seconds, the strip will adhere to the epoxy droplets E, by means of the adhesive C, providing a wide-area of adherence.

To prevent damage of protein samples upon attachment, the sample strips need to be kept wet during the procedure. This can be done either by rapid manipulations using water or buffer solution or by adding 10% sugar or glycerol solutions to the intermediate holder with protein sample. Upon use of the gluing procedure, the sample must be allowed to stand for 5–10 min to enable cyanoacrylate polymerization. Before sample detachment from the surface of the intermediate holder, a water droplet should be applied over the sample to allow for easy detachment of the sample strip from the surface of the intermediate holder.

Figure 11A:
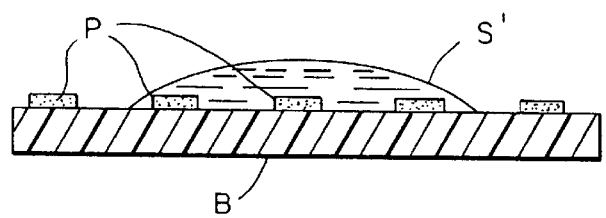
FIGS. 11A–11D are schematic cross-sectional views showing the process of preparing strips.
Figure 11B:
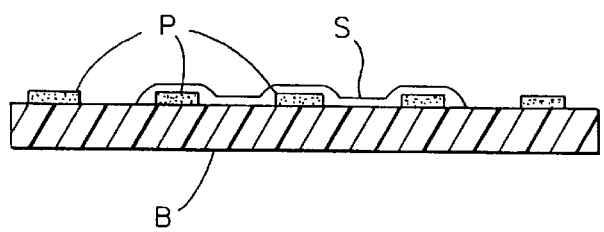
Figure 11C:
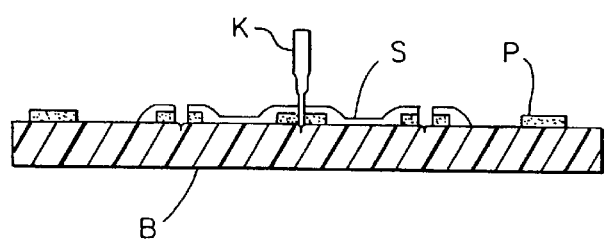
Figure 11D:
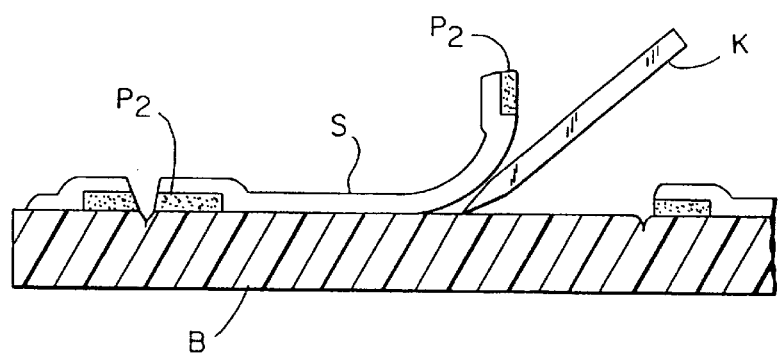

FIGS. 11A–11D show the method of the invention for preparing end-reinforced strips S. In the cross-sectional views of FIG. 11, reinforcement strips P are laid out over base B of glass, plastic, or other smooth-surfaced material. The strips P and base B are then wetted with a solution containing protein or DNA. As in the prior art method shown in FIG. 1, the solution is vacuum-dried, cross-linked, and perhaps washed. After these preliminary steps, the reinforcement strips P are covered with a film of protein or DNA material for the strips S, as shown in FIG. 11B. A knife K is then used to split each reinforcement strip lengthwise, as shown in FIG. 11C, forming two strips $P_2$ from the one strip P. After this, the strips may be trimmed to length in the cross direction (not shown), if need be. Finally the finished strips S are peeled away with the knife K, as shown in FIG. 11D.

A preferred material for the reinforcement strips P is baked gelatin. The strips are formed on the base B, preferably by photolithography. Gelatin, made photosensitive by the addition of ammonium dichromate, is used. After dissolving unexposed gelatin, the remaining strips are baked in an oven at 180 degrees C for two hours. The surface of the substrate base B was finally subjected to 20 seconds of plasma discharge at reduced air pressure to permit strong adhesion of the protein layer to the reinforcement strips P.

The present invention contemplates not only sample strips formed by drying of a solution, but also samples formed by other methods and in shapes other than flat bands or strips. The invention also includes sandwich-like samples having surface layers made of or containing one protein or other substance to be tested for ligand bonding, and an internal layer of another substance that is not exposed to the ligand solution.

Another preferred method of preparing a sample strip (film) for use in determining ligand binding to protein or nucleic acid molecules is an electrospray (ES) method where electrostatic atomization of a liquid or a solution is used to obtain charged microdroplets or charged ions for deposition on a surface. The solution or liquid of substance to be deposited is placed into a capillary, and the application of high voltage results in instability of the liquid or solution, which is then dispersed into small charged droplets typically 0.5–2 microns in diameter. Electrostatic repulsion rapidly moves these charged microdroplets from the capillary tip, and in their travel toward a substrate surface, the microdroplets evaporate if solvent vapor pressure is low enough and reach a Raleigh limit of electrostatic stability. Afterwards, the microdroplets undergo a series of decays, reducing their size to 10–20 nm and increasing the electrostatic field to a level where evaporation of ionized solvated molecules becomes possible. On further travel through a dry gas these solvated ionized molecules lose the solvents. Where evaporation proceeds rapidly, all of the solute content of the microdroplets can be concentrated into small nanoclusters.

Techniques of electrospraying biologically active materials, some of which are applicable to the application of the present invention, are discussed in detail in a U.S. provisional application of the present inventors entitled "Method of Electrospraying Solutions of Substances for Mass Fabrication of Chips and Libraries", filed on Jun. 20, 1997, the entire contents of which are hereby incorporated herein by reference.

Electrospray, which occurs in a humid atmosphere or where the electrospray source is at a short distance from the substrate (target) surface for deposition, can allow microdroplets to reach the substrate surface without decay or production of ions. This regime is referred to as wet electrospray (WES). The deposition of charged molecules or clusters occurs in a dry electrospray (DES) regime where the conditions of dry air or a longer distance between the electrospray source and the substrate surface is used.

Accordingly, this electrospray phenomena permits the deposition of substances in the different forms of charged microdroplets, solvated or dry ionized molecules, or nanoclusters. The form of deposit can be regulated by changing the travel path of the charged species, by control of vapor pressure in atmosphere, and by proper choice of solvent and solution concentration.

One of the earliest applications of electrospraying was in the production of thin sources for radioactivity measurements. This earliest application and other applications of electrospraying, such as paint spraying, pesticide spraying, and use as a source of ions for mass spectrometry of biological molecules, are reviewed in Michelson, D., *Electrostatic Atomization*, IOP Publishing, New York, N.Y., 1990. Electrospraying of biological molecules was developed for use with mass spectrometry to characterize the structural features and non-covalent interactions.

The method of preparing a sample film according to the present invention uses a mask having a non-round hole interposed between an electrospray source and the substrate surface on which a film is to be deposited. Thus, the charged microdroplets, clusters or ions can be directed through a hole or an array of holes in a mask and onto a substrate surface.

Figure 31:
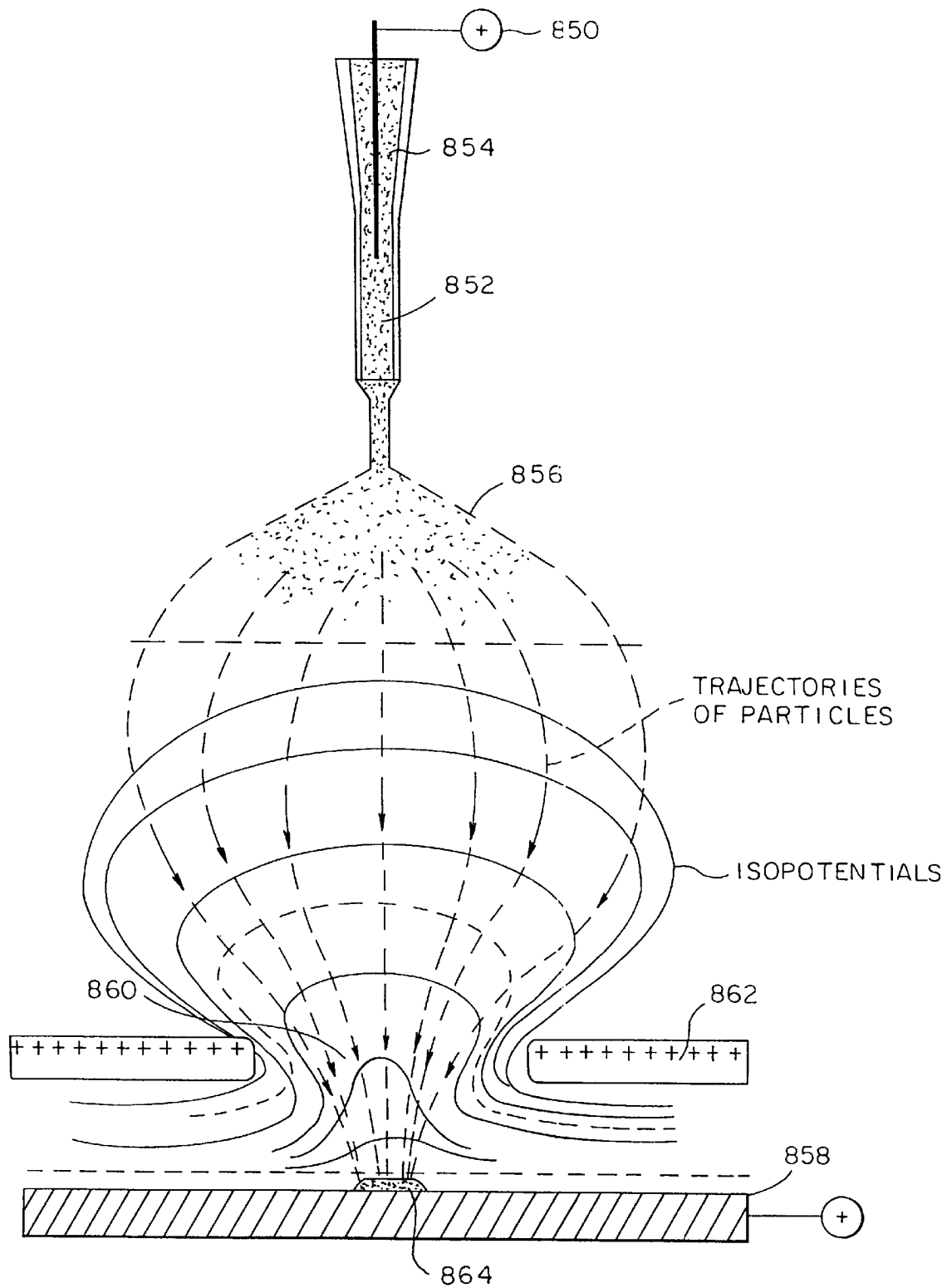
FIG. 31 schematically illustrates the electrostatic lens effect in the electrospray deposition of charged particles through a hole in a dielectric screen.

When electrospray deposition is performed through a thin conducting mask under the same potential as the substrate and positioned in close vicinity to it, the deposits exactly follow the form of the hole in the mask with sample biomolecules uniformly distributed over the deposit. However, much of the biomolecules in the sample are deposited and lost onto the mask itself, thereby making this configuration of the electrostatic field for electrospray quite ineffective and time consuming.

It was further discovered that when the mask is under a potential of the same sign as that of the electrospray source and microdroplets, the preferential deposition of electrosprayed material onto the substrate is very efficient because the charged mask repels the electrosprayed material and changes their trajectory so that they pass through the hole(s) in the mask (screen). This electrostatic lens effect as discovered with a charged plastic or metal screen under conditions of ambient air or in any gas phase under normal pressure is illustrated in FIG. 31, and is based on the deviation of trajectories of charged particles in an uneven electric field in the vicinity of the hole. As shown in FIG. 31, an electrode 850 with a positive charge disposed in a capillary 852 destabilizes a solution of biomolecules 854 which is electrosprayed from the capillary tip as a torch 856 where the trajectories of the particles (as represented by the arrows) towards the substrate 858 are deviated and focussed through a hole 860 in a charged screen 862 used as a mask to deposit a spot (film) 864. The uneven electric field protruding through the hole(s) forces charged particles to move normal to isopotential lines, which then enables the material to be deposited as a spot having a size smaller than the hole in the mask.

It is noteworthy that the operation of this electrostatic lens is different from that in electronic microscopes because the inert forces which determine the trajectories in vacuum electrostatic lens are negligible in air under normal conditions where viscous forces dominate This electrostatic lens effect has the advantage that the size of the deposit is substantially smaller than the hole in the mask. Another advantage is that the electrosprayed material is deposited with close to 100% efficiency since the screen adsorbs only a small fraction of the charged molecules.

The mask used in electrospray deposition of a sample film has a hole and is positioned between the electrospray source (capillary) and the target. The mask can be a screen that is preferably made from a non-conducting material, where the concentrating electrostatic lens effect is automatically achieved when the first charged molecules of the electrospray are adsorbed onto the screen surface, thereby electrostatically blocking any further adsorption of charged molecules. The non-conducting screen with a layer of adsorbed charged molecules then serves to direct all the charged molecules of the electrospray into the hole of the screen for deposition onto a substrate.

Conducting screens, such as metallic screens, can also be used as a mask. However, the potential on the conducting screen used according to the present method of preparing a sample film should be adjusted to be intermediate between the potential on the electrode in the capillary and the potential on the substrate in order to direct the charged molecules into the hole.

It was also discovered that electrofocussing is not observed with a single hole (i.e., rectangular or non-round hole used for preparation of a strip of sample film) when the electrospray source is not positioned directly over the hole and the substrate and mask are rotated together around the normal axis through the center of the hole in the mask. The size and shape of the deposit conforms to the size and shape of the hole under these conditions.

The degree of electrofocussing is affected by the distance between the capillary tip and the screen, thickness of screen, etc. In general, the thicker the screen or the farther apart the screen from the capillary, the better the degree of electrofocussing.

Any relative motion of the capillary and the substrate compatible with the condition of spending equal time over each area of deposition on the substrate would provide uniform deposition and can be determined by those of skill in the art. For the deposition of a non-round film, such as a rectangular or extended ellipsoid strip with an uniform thickness to be deposited, the capillary is preferably stationary and not positioned directly above a non-round hole in a mask while the mask and the substrate/support are being rotated. In this way, the rotating mask and substrate/support bypass the electrostatic focussing effect of the hole by allowing charged particles to approach the hole from the side. As a rule, a guard ring having a potential of the same sign as the charged microdroplets leaving the capillary tip is positioned below the capillary tip to surround the zone of electrospray discharge with a charge that repels the charged microdroplets and prevents any scatter during electrospray.

In order for biomolecules such as proteins and DNA to retain their structural and functional properties when electrosprayed as a film onto a substrate/support, the strength of the electric field at the capillary tip of the electrospray source is to be sufficient for effecting electrospray but not so high as to result in corona discharge, which destroys the functional properties of the biomolecules. The strength of the electric field at the capillary tip can be controlled by maintaining a constant current or a constant voltage to discharge the solution in the capillary. The minimum voltage or current is empirically determined. It was discovered that the minimum voltage that enables an effective electrospray is dependent on the radius of the capillary, solution conductivity, flow rate, and the distance between the capillary and the substrate. With a capillary diameter of about 20–30 microns, and the capillary to substrate distance of about 15–20 mm, a protein solution is electrosprayed very effectively at 2–4 kV with a flow rate of 50–200 nanoliters/min. Above 6 kV, the properties of the biological molecules are likely to be destroyed in the electrospray process. Replacement of air with freon or other corona-suppressing gas can be used to help prevent corona discharge. Corona discharge effects can also be inhibited if electrospray is assisted by air-jet atomization, from which micron-sized droplets can be obtained at considerably lower voltages than needed for electrospray alone. Jet-assisted electrospray also accelerates the deposition of material since stable dispersion can be obtained at much higher flow rates than with electrospray alone.

The substrates or supports onto which the charged particles are deposited preferably have a high conductivity. However, other materials with low bulk conductivity (semiconducters) or those having small surface conductivity can also be used as substrates. Examples of such materials include hydrophilic plastics, PVDF (e.g., IMMOBILON-P) and nitrocellulose membrane filters, mica and glass. Mica is nonconducting when dry but has surface conductivity when wet or in a humid atmosphere.

In one embodiment of the method of preparing a sample film according to the present invention, electrospray deposition onto a nonconducting surface, such as a mica surface, is performed by periodical recharging of the nonconducting surface with a stream of counter ions from a corona discharge. The stream of counterions is generated with an array of microelectrodes in a shielded chamber. Such recharging provides the advantage that successive layers of charged molecules can be deposited onto the substrate by repeated cycles of spray and recharging; otherwise, a buildup of charged molecules on the substrate would prevent further deposition. In the example of a mica surface, a mica sheet is placed on a rotating plastic disk and periodically recharged during its period of rotation that passes underneath an array of microelectrodes. Both positive and negative voltages can be applied to the capillary with respect to the mica. To reduce the surface conductivity of the mica, the mica surface can be kept dry during deposition by heating with an infrared source or with a stream of dry warm air. Deposition can be performed for example in open air or in a chamber with a controlled atmosphere.

In a preferred embodiment for preparation of a sample film for using in the apparatus and methods of the present invention, an intermediate layer between the substrate and the sample can be introduced to facilitate the detachment of the deposited material as a sample film from the substrate or support, i.e., for transfer to a measuring device using such a sample film. Such an intermediate layer must be slightly conductive and must be easily removable after cross-linking of the electrospray-deposited biomolecules. Examples of materials which can be used as an intermediate layer include: (1) a water-soluble polymer layer, such as polyacrylamide or polyethylene glycol which slowly swells and dissolves in the presence of water and/or other conditions, i.e., pH; (2) a layer of a commercially available polymer having disulfide bonds which can be broken (chemically reduced) when in contact with a mercaptoethanol solution, thereby resulting in dissolution of the polymer; (3) a layer of highly dispersed carbon with low adherence to the deposited biomolecules; and (4) a layer of carbon-polymer conducting composites with a low melting point.

Figure 32:
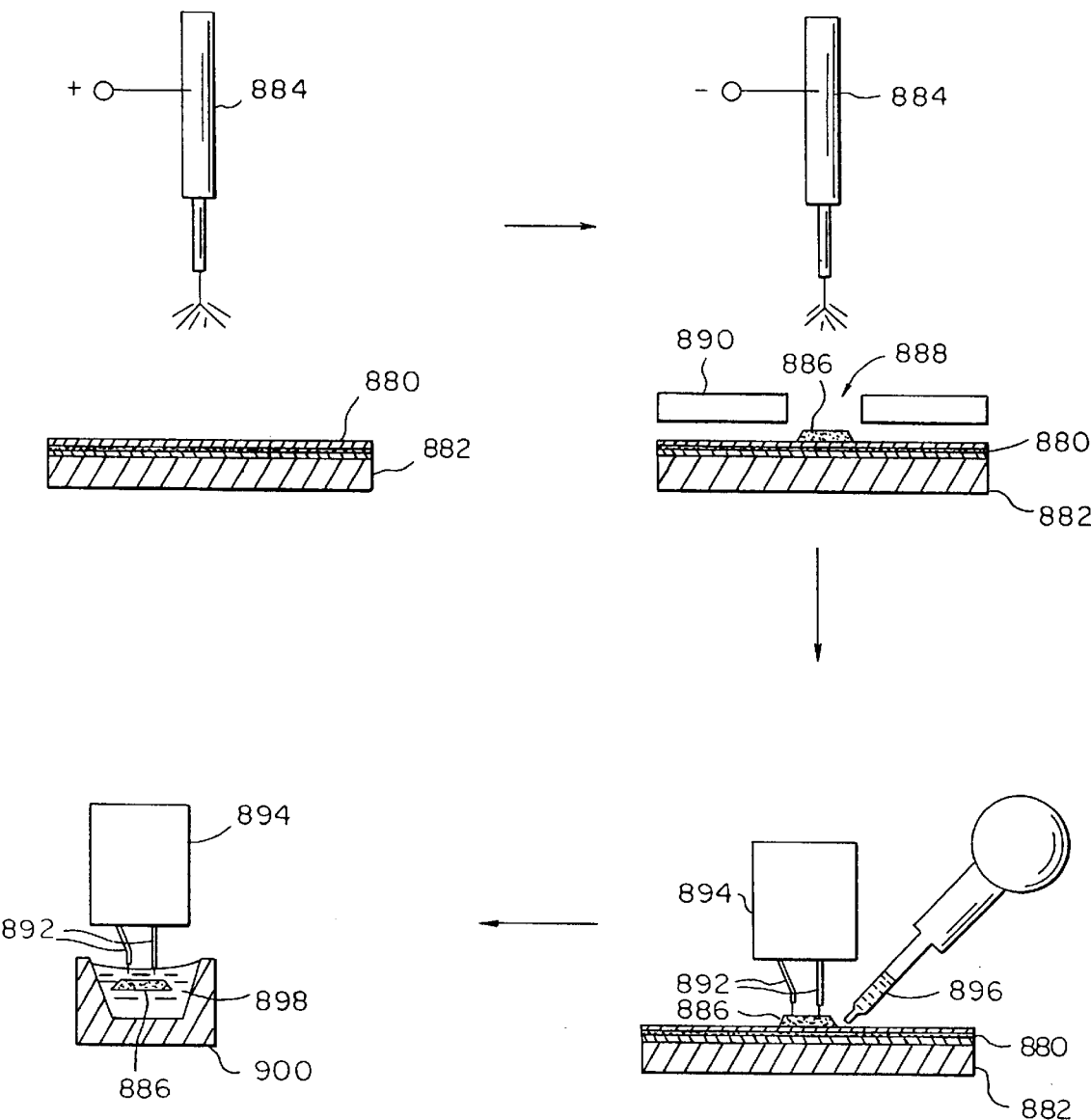
FIG. 32 is a schematic of a process for the fabrication and detachment of a sample film.

FIG. 32 schematically illustrates an embodiment of a process for the fabrication of a sample film on an intermediate layer and the detachment therefrom. A semiconductive sublayer 880 as an intermediate layer is first deposited over a conductive substrate 882 by electrospray with a capillary 884 or by any other known methods and then a sample film 886 of the desired biomolecule(s) is deposited by electrospray through a hole 888 in a mask 890. The sample film can be attached to the tips 892 of the apparatus of the present invention 894 and detached from the substrate by dissolving the semiconductive sublayer with a solvent 896 and then immersing the sample film 886 into a solution 898 in a flow cell 900. Alternatively, the sample can be simply lifted off the substrate as a detached film.

A preferred intermediate layer for the detachment of the sample film is a sublayer of alginic acid which is insoluble to solutions with an acidic pH but can be readily dissolved with a solution at an alkaline pH. It will be appreciated by those of skill in the art that the use of an intermediate layer (sublayer) to facilitate the detachment of the sample film is not limited to an electrospray-deposited sample film. Such an intermediate layer is equally useful to facilitate the detachment of a sample film that is applied as a solution on top of the intermediate layer.

Using protein as an example of a biomolecule for electrospray deposition, the structure of the protein film and the functional properties of the protein molecules in the film is dependent on the path of flight of the electrospray and the humidity and temperature under which the protein molecules are electrosprayed. At short distances, e.g., about 15 mm between capillary and substrate, or when the electrospray takes place in a humid atmosphere, charged microdroplets from the electrospray can reach the surface without decay or the production of ions in the wet electrospray regime. The protein films obtained after evaporation of the deposited microdroplets on the substrate have much in common with the protein films obtained conventionally by applying a solution of proteins directly to the substrate and allowing the proteins to dry. No notable difference in the mechanochemical response to ligands, such as $Ca^{2+}$, glucose, and NADH, was detected between films of a-lactalbumin, yeast hexokinase, and horse liver alcohol dehydrogenase, respectively, prepared by wet electrospray deposition onto a glass surface covered with a conducting $SnO_2$ layer and films of the same enzymes prepared by the conventional method.

The electrospray deposition of biomolecules can be used as a means of not only obtaining a sample film, but also of concentrating microquantities of dilute biomolecule solutions. Above about 70–80% humidity, microdroplets are deposited by electrospray and the effect of concentration may not be significant. At lower levels of humidity, concentration of biomolecules in microdroplet form can occur and the conditions can be adjusted for electrospray, i.e., longer distances, dry conditions, where nanoclusters and ions of biomolecules are deposited onto the substrate. In dry electrospray, biomolecules are deposited as single molecules only if the concentration in solution is below a critical threshold of about $10^{-3}$–$\mathbf{10^{-5}}$ mg/ml. At higher concentrations, the dry electrospray deposition of proteins and other biomolecules occur mostly in the form of nanoclusters.

Besides the faster drying achieved in dry electrospray, which helps protect proteins from damage, addition of protective reagents such as carbohydrates, e.g., glycerol, sucrose, trehalose, etc., also serve to provide protection against damage and/or inactivation upon drying. When electrosprayed under mild conditions of low voltage/current and controlled humidity, the presence of sucrose protected the activity of an alkaline phosphatase (AP) enzyme relative to AP directly dried onto the same substrate from the same solution used for electrospray. The specific activity of the AP enzyme deposited by electrospray under mild conditions was found to be similar to the initial enzyme solution. For proteins with free SH- groups that are essential for their functional properties, such as in hexokinase, the presence of β-mercaptoethanol, a reducing agent which protects the oxidation of SH- (sulfhydryl) groups in the electrospray solution, was found to result in a considerable increase of the mechanochemical response of the electrospray-deposited protein film.

In addition to protecting biomolecules against damage during drying in the method of preparing a sample film according to the present invention, protective reagents, such as the carbohydrates and polyols, e.g., glycerol, sucrose, trehalose, etc., can also serve to decrease the packing density of biomolecules, particularly proteins, in the deposited sample films. These protective reagent additives are water-soluble and non-volatile. After the biomolecules in a dry state are cross-linked, the water-soluble and nonvolatile additives can be washed away and thereby create additional voids and channels in the sample, thus lowering the packing density in the cross-linked sample film and enhancing the penetrability of the sample film to ligands.

Another way of decreasing the packing density and enhancing the penetrability of a biomolecule sample film is to use dry electrospray with high concentrations of biomolecules in solution, which results in the deposition of biomolecules in the form of nanoclusters. The size of the deposited nanoclusters strongly depends on the biomolecule and solute concentrations. The internal diffusion in such films composed of the electrospray-deposited nanoclusters would be much faster since the large intergrain channels are easily penetrable by ligands, and only the diffusion within the grains will be slowed down to the level of a homogeneous film.

While it is expected that large ligands can also penetrate sample films having a low packing density as described above, the reduction of the thickness of the deposited biomolecule film layer to the thickness of about a monolayer on a substrate surface avoids any diffusional limitations in the sample film. The molecules in the monolayer are cross-linked to a substrate surface as well as cross-linked to each other. The substrate for a deposited monolayer film is preferably a material, i.e., gel, which does not restrict the flexibility of the monolayer film. Other such suitable materials are well within the knowledge of those in the art.

Agents that are available for cross-linking biomolecules together are well-known to those of skill in the art (Hermanson et al., *Immobilized Affinity Ligand Techniques,* Academic Press, New York, 1991). UV irradiation can be used for DNA molecules. For protein molecules, glutaraldehyde is preferred because it has advantages in terms of preserving the functional activity of cross-linked proteins. Glutaraldehyde attacks free amino groups, which are numerous in protein molecules, and their modification does not appear to adversely affect the functional properties of proteins unless the amino groups are directly involved at an active site. While the amino groups at active sites can be protected from reaction with glutaraldehyde by the steps of reversible maleilation at basic pH, cross-linking under basic pH, and deblocking by storage at slightly acid pH (pH 5–6), the laboratory of the present inventors has found that ligand binding, as determined by affinity assays performed on this film, was still detectable even if the amino groups were left unprotected in proteins which have amino groups in their active sites, i.e., ribonuclease, monoclonal antibodies, etc. It is useful, however, to protect the amino groups when the protein has either numerous free amino groups or amino groups in a binding site so as to obtain a larger signal-to-noise ratio.

Before the cross-linking of the deposited biomolecules, and in particular proteins, the film of biomolecules may be exposed to either a humid atmosphere or a solution, i.e., a glycerol solution, which allows for limited mobility or liquidity of the biomolecules in the sample film but not for solubility in the solution. The effect of increased liquidity allows the protein molecules in the film to move relative to other protein molecules in the film to provide a film with no visible inhomogeneity. This phenomena can be likened to big round rocks that are haphazardly dumped onto a surface which results in an inhomogeneous topography. If the big rocks are allowed to move relative to one another due to some form of disturbance, then the big rocks would preferably move to a more uniform topography. A homogeneous film of proteins however provides strength at the expense of possibly reduced ligand penetrability.

The method of preparing sample films according to the present invention can be used to fabricate sensitive elements of biosensors from very small quantities of proteins (0.1–1 microgram). This is especially important when applied to a mechanochemical method of testing the biospecificity of protein molecules by change in the properties of a protein film, since microgram quantities of proteins are usually readily available from common analytical scale protein purification procedures, such as electrophoresis. The method can also be used to prepare protein film for other types of biosensors, e.g., enzyme electrodes, MOSFET chemosensors, biosensors based on changes in mass or in the optical properties of the protein film, etc.

An example of the preparation of such a sample film is presented in FIG. 32, where the electrospray deposition is used to obtain a single sample film of immobilized protein for mechanochemical testing of protein bioaffinity. The method according to the present invention enables the fabrication of protein samples from microgram amounts of protein dissolved in a few microliters of water. To allow easy detachment of the sample, a sublayer, as shown in FIG. 32, is predeposited on a conductive substrate.

Direct binding detection methods using the sample film deposit include plasmon resonance (i.e., elliptical reflectance microscope, which is commercially available) and scanning probe microscopy (force microscope may be used to discover the binding of ligands to an array of sample films of large protein molecules on a substrate surface, whereas tunneling microscopy may be used in the detection of binding of DNA probes to complementary oligonucleotides present in matrices on a substrate surface).

Referring again to FIGS. 4 and 5: With a sample strip S mounted between the tips of the arms 148, 168, and reference solution L flowing in the well 210, mechanochemical testing of the sample S is ready to begin. Testing itself consists of two stages. In the first (preparative) stage, the strip is stretched until a maximum spring constant of the strip is obtained, and then is allowed to relax under isometric conditions until a constant level of isometric tension is reached. Isometric condition herein means keeping a fixed distance between tips of the arms 148 and 146. In the second stage relaxed strip is brought into contact with ligand solution and ligand-induced changes of the isometric tension and spring constant are measured.

In the first stage the strip is stretched by fixed strain $$\epsilon_0 = (L - L_0)/L_0$$

where $L_0$ is the strip length in the reference solution when no tensile force, is applied, and L is the strip length in the same solution under a load F.

According to known Hooke's law to obtain the strain one needs to apply stress $$\sigma = F/bh = \epsilon_0 E$$

where E is Young's modulus of the protein material, b and h are the width and thickness of the sample. Thus, $$F = \sigma bh = bh\epsilon_0 E = bhE(L-L_0)/L_0$$

Theoretically force should grow proportionally to $(L-L_0)$, however, practically the last relationship does not work at the beginning of stretching, when the strip is not completely stretched and when it stretched to a large extension, where destruction of the strip can occur. To achieve maximum sensitivity the highest F should be used that does no damage the sample. It has been found that the most convenient way to find this load is to measure spring constant of the strip during the stretching. The spring constant is small in the unextended strip, and it drops drastically when strip damage begins to occur at large extensions. A maximum spring constant occurs between these two extremes.

Spring constant is measured by applying small deformations to the strip with an amplitude AL much smaller than $(L-L_0)$. These deformations cause tension oscillations with amplitude of $\Delta F$. Spring constant of the strip is defined as $$\kappa = \Delta F/\Delta L.$$

The inverse of spring constant is defined as sample compliance.

In order to obtain a good measure of the sample spring constant, the sample's compliance must be much larger than sum of the compliances of force transducer and the block of sample deformation.

Young's modulus is related to the spring constant with the formula $$E = \kappa L_0 / bh.$$

At the testing stage, ligand-induced changes in F and κ are measured after an exchange in the flow cell of reference solution for that containing ligands. These parameters by themselves can be used to detect binding. However, they also allow estimation of a practically important parameter: ligand-induced strain, $\epsilon L = (L - L_1)/L_0$, where $L_1$ is the length of the sample in the ligand solution when no force is applied. This can also be calculated by the formula $$\epsilon_L = -\epsilon_0((\Delta F/F) - (\Delta \kappa / \kappa))$$

where Δκ is measured change in the spring constant.

The compliance is measured typically at low frequencies of 0.1–0.15 Hz, well below any resonant frequency of the arms 148 or 168.

The electronics 199 in FIG. 4 include all the various conventional circuits and devices that are adapted for using the transducers of the present invention in testing sample strips S. Examples of such devices are power supplies; voltage regulators; frequency generators, analyzers, and converters; amplifiers; computers; recorders; A/D or D/A converters; DC and AC voltmeters and ammeters; oscilloscope-type display instruments; and related devices. This list is exemplary only, and the invention may include other kinds of electronics.

Air conditioners or supplies for blowing air over the transducers, heating/cooling units, pumps, chemical equipment, and vibration isolation equipment are also contemplated as part of the invention.

The tests described in the present example are of two kinds. In the first, the sample was strained a predetermined amount, e.g., 1.5% to 4.0%, and the tensile force F was measured as the dependent quantity. In a second kind, the Young's modulus according to the dynamic definition was the quantity measured. The present inventors found that both quantities were very useful in detecting binding of ligands to proteins or DNA. Those of ordinary skill in the art will be aware of other tests which can be conducted using the apparatus of the present invention.

The apparatus of the present invention, preferably with the accessories described, might be immediately used in any study of interaction of small ligands with protein or DNA molecules. Possible applications include the following:

1. It is known that certain extracts contain a compound active against a known target protein. An easy way to rapidly find and isolate the active component is to attach the device, with the sample made of this protein, to the output of an HPLC or other chromatograph, when running the extract through it.

2. The present invention may be used in massive primary screening of compounds for their interactions with important protein (or DNA) molecules when searching for potential drugs.

3. The invention may be used in the primary analysis of the biohazard of newly synthesized compounds. Samples made of key enzymes and other proteins may be tested as possible targets of these compounds. For example, all compounds binding acetylcholine esterase with high affinity may be suspected as possible poisons.

4. The invention may also be used in biochemical analysis of metabolic control in living cells. Allosteric effectors of key metabolic enzymes may be discovered by applying all possible metabolic intermediates to samples made of a few key enzymes.

5. The device of the invention may be also used as a chemosensor to measure the concentration of a certain compound in liquid samples. It has the advantage, as compared with other biosensors, that the same measuring unit may be used with any specific activity given by specific samples. The sensitive elements for the sensors may be fabricated and supplied separately to consumers upon their request.

6. The device can also be used in studies of muscles and other biological tissues, where mechanical properties, such as contractility, are strongly connected with their biological function.

7. The invention may be used for analysis of certain components in water. This may be done either in a regime of monitoring, when measurements are made by certain intervals, or only detachable samples can be exposed to water for a given period of time, and then analysis of the residual capacity to respond to the ligand may be tested and compared with control samples. Thus, the binding procedure and the reading of the result may be temporally and spatially separated.

8. Analysis of air pollution with the device is also possible, as well as direct analysis of extracts in organic solvents.

Rather than immersing the sample in a solution for the purpose of testing in accordance with the present invention, the sample held between the tips of the apparatus of the present invention may be placed into a gaseous atmosphere to be tested. Thus, ligands or chemicals in vapor or gaseous form can also be tested by means of the present invention.

While the preferred sample material in accordance with the present invention is a film of protein or nucleic acid material, the present invention can also be used to test the effects of chemicals on other polymeric materials. For example, some polymers are known to respond mechanically to the presence of certain chemicals in the atmosphere or in solutions by swelling (such as in solvent vapors) or by reducing elasticity or tensile strength (classic example, weakening of a rubber strip in the presence of traces of ozone in the air). Similarly, the apparatus can be used to study microscopic polymer samples for their stability in certain environmental conditions, ability to absorb substances, etc. All of these possible uses are also comprehended within the scope of the present invention.

Having now generally described the invention, the same will be more readily understood through reference to the following examples which illustrate specific tests conducted using the methods and apparatus of the present invention and which are provided by way of illustration. These examples are not intended to be limiting of the present invention.

EXAMPLE 1

Figure 12:
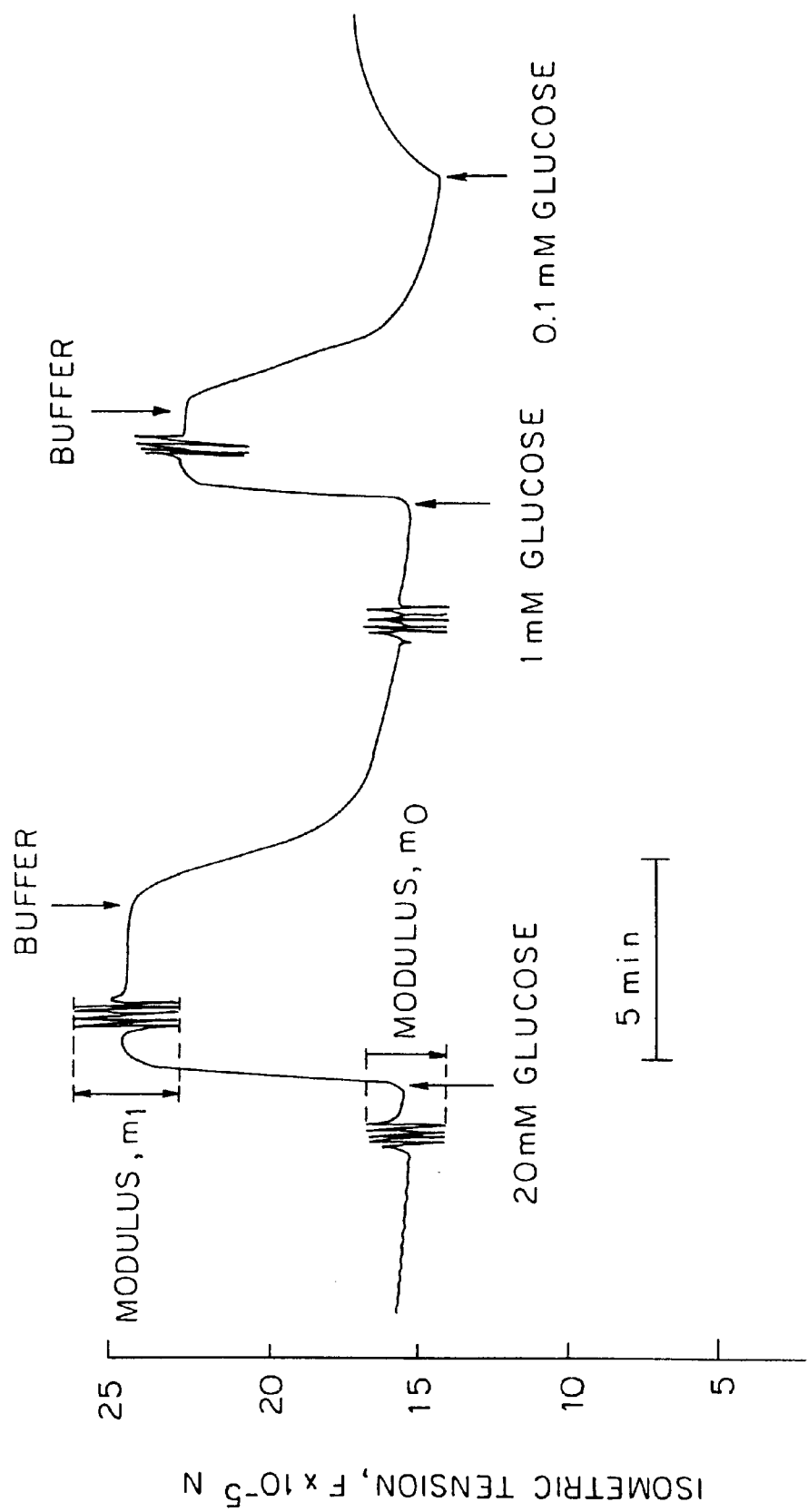
FIG. 12 shows the measurement of changes in isometric stress and elastic modulus of a hexokinase sample in response to different glucose concentrations.

A film of yeast hexokinase (Sigma Chemical Company, St. Louis, Mo.) was prepared. The preparation was like that described in Morozov and Morozova, *Anal. Biochem.* 201:68–79 (1992) and *FEBS Lett.* 175:299–302 (1987), except that sucrose was added to the protein solution in amount 30% by dry weight to prevent cracking of the sample strip S. A strip measuring 800 μm by 100 μm was cut and mounted on the arms 148, 168 and extended 2.8%, reaching the maximum value of elasticity, and then allowed to relax for 20 minutes. After relaxation of the sample in the reference buffer glucose solutions prepared on the same buffer were introduced into the well 210. Changes in elasticity and isometric tension in the sample were measured at the moments indicated by arrows and changes in tension and in modulus resulted from such exchange of solutions were measured. The results are shown in FIG. 12. The buffer used is 10 mM HEPES, pH=7.5, 0.1 NaCl.

Figure 14:
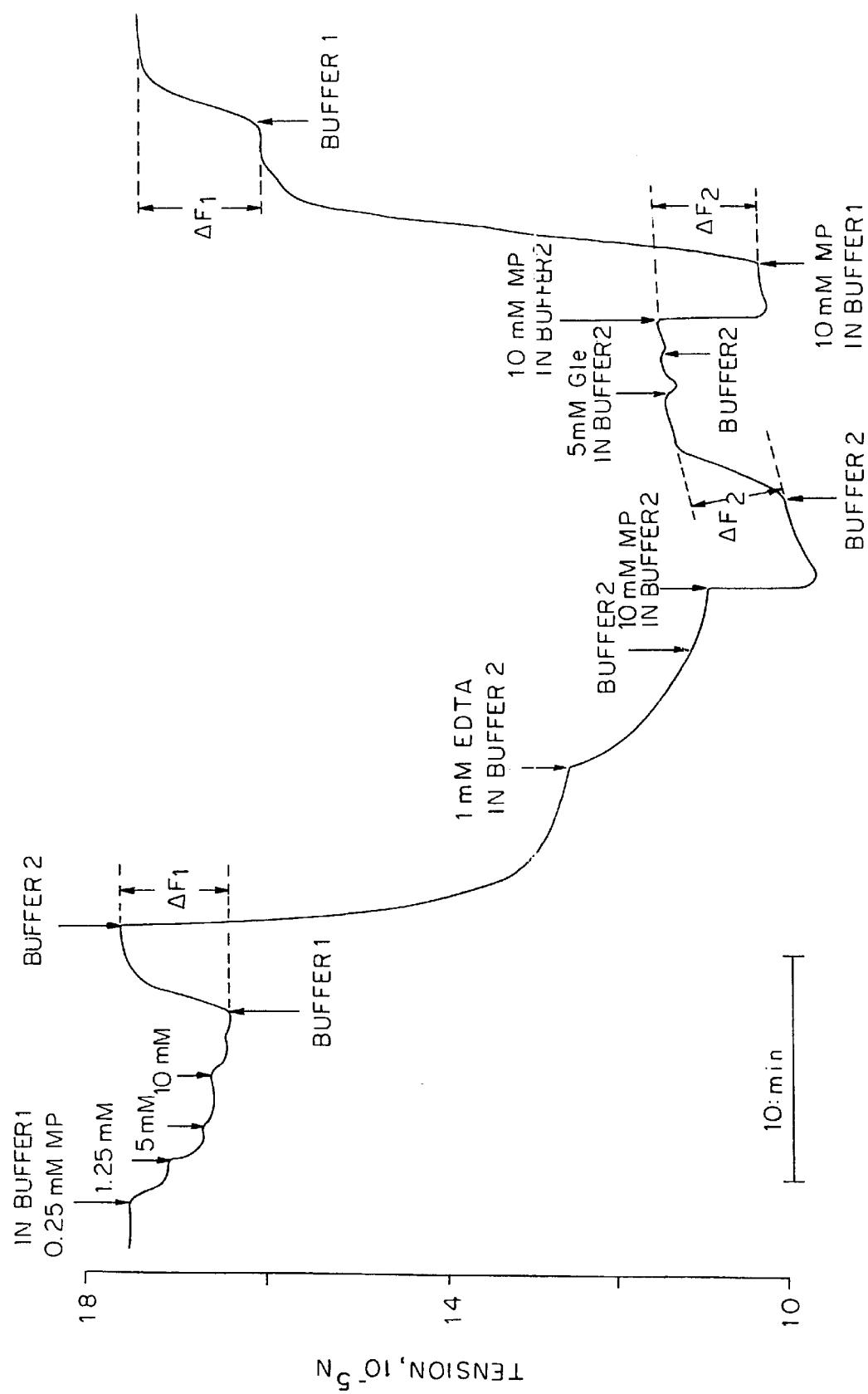
FIG. 14 shows the measurements of changes in isometric stress of a concanavalin A sample in response to different concentrations of methyl-α-D-mannopyranoside (MP), to glucose solution (Glc) and to removal of divalent cations from buffer solution.
Figure 16:
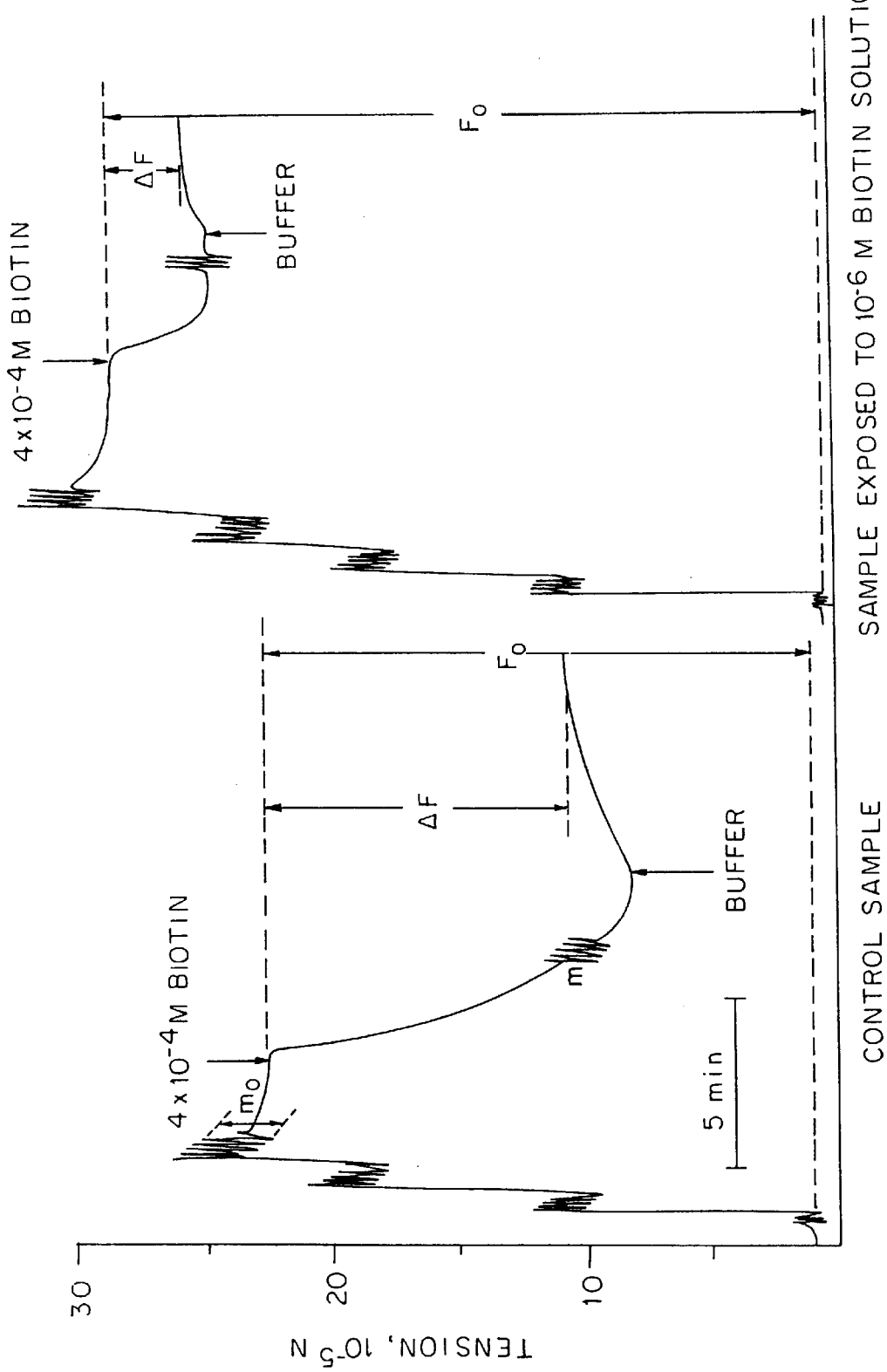
FIG. 16 shows the procedure of testing of response of avidin film to biotin solution in control sample and in sample preexposed to $10^{-6}$ M biotin solution for 48 hours.

Ligands are added at the moment indicated by arrows in FIGS. 12, 14, and 16.

This graph shows that varying the glucose concentration caused large but reversible changes in the hexokinase sample's isometric tension and compliance; reversibility is shown by the graph's return to the initial state after buffer solution is introduced. The steady-state, horizontal line elevations indicate the tension in the sample strip. The oscillations show the compliance measurement, in which the strain and the resulting stress are varied sinusoidally. The amplitude of the oscillation is a measure of the compliance. This example illustrates that known specific interaction of hexokinase with its substrate, glucose, can be detected in few minutes using the present invention.

Figure 13:
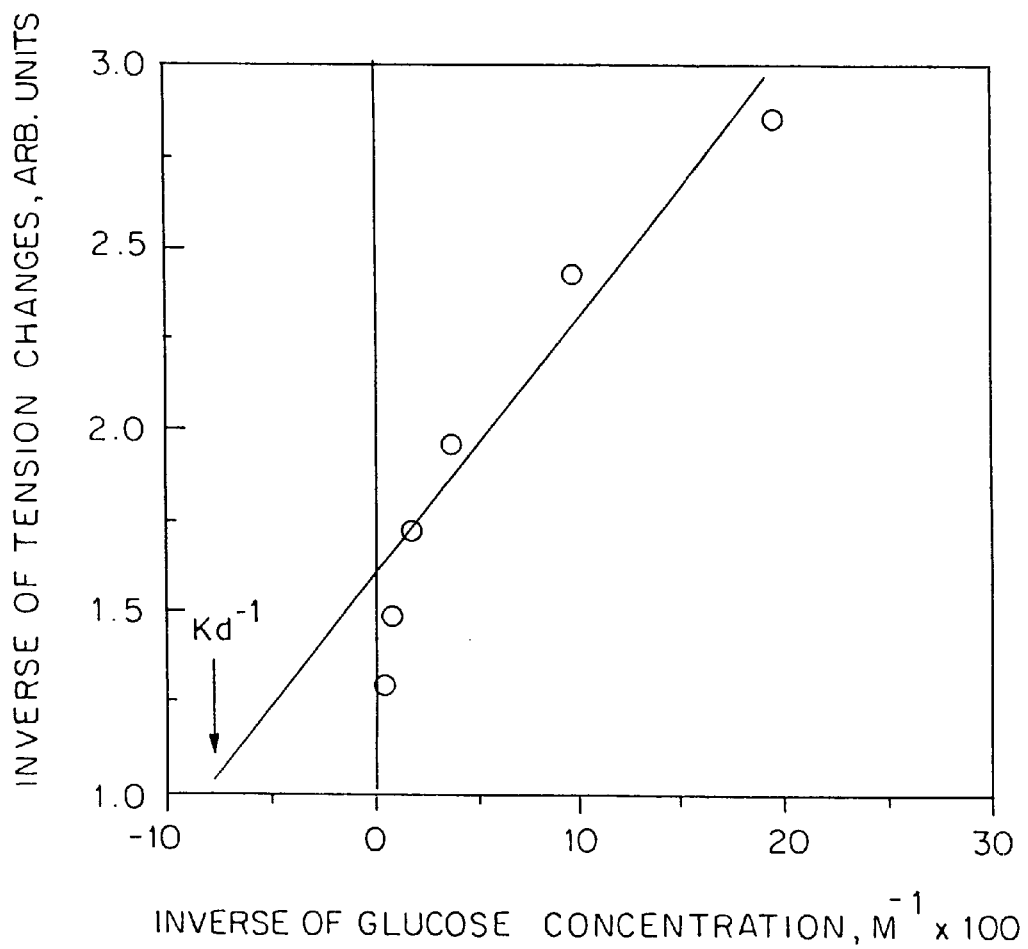
FIG. 13 shows the determination of dissociation constant for glucose in hexokinase protein film.

FIG. 13 is a graph of inverse tension changes against inverse glucose concentration, showing a linear relationship.

As shown in FIG. 12, the amplitude of tension changes in response to glucose solutions depends on their concentrations. This allows estimation of binding constant to characterize affinity of glucose to the hexokinase. An example of such estimation is presented in FIG. 13. Here a graph of inverse tension changes against inverse glucose concentration (Lineweaver-Burk plot, see L. Stryer, Biochemistry, W. H., Freeman and Company, New York, 1988, pp. 189–190) is presented showing a linear relationship. This indicates that glucose-hexokinase interaction is described by the well known Langmuir isotherm and dissociation constant of the glucose-hexokinase dimer under similar conditions (Mayes et al., *Eur. J. Biochem.* 133:127 (1983)).

EXAMPLE 2

Figure 15:
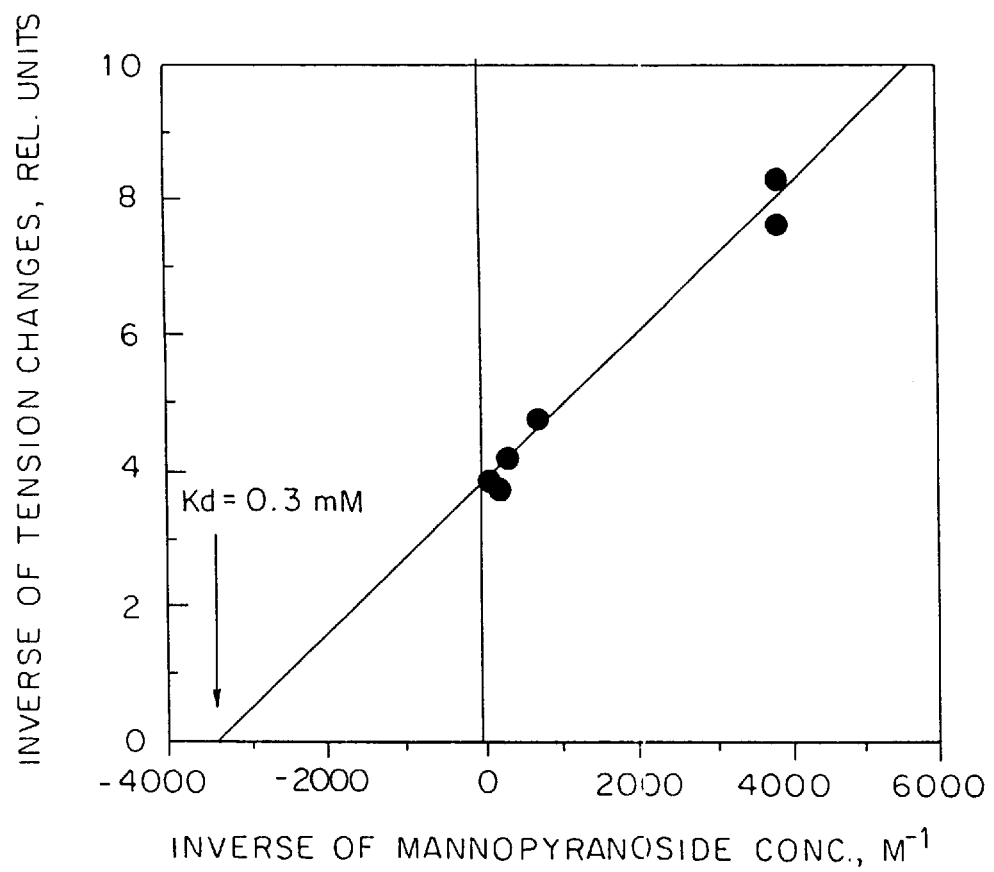
FIG. 15 shows the determination of dissociation constant for methyl-α-D-mannopyranoside in concanavalin A protein film.

A strip of concanavalin A, (Sigma, St. Louis, Mo.) was prepared as described in Example 1 for hexokinase, mounted on the arms 148, 146 and extended by 1.2% in buffer 1 (10 mM HEPES buffer, pH=7.5, containing 0.1 M NaCl and 0.1 mM $MnCl_2$ and $CaCl_2$ each). After relaxation solutions with 0.25 mM, 1.25 mM, 5 mM and 10 mM of methyl-α-D-mannopyranoside (MP) on the same buffer 1 were introduced into the well 210 at the moments indicated by arrows in the FIG. 14. Addition of each other solution is seen to reduce progressively the isometric tension in the concanavalin A strip. Lineweaver-Burk plot of these tension changes similar to that made in Example 1 for hexokinase (FIG. 13) allows determination of dissociation constant of MP. This plot for concanavalin is presented in FIG. 15 and gives $K_d=0.3$ mM. This value is close to the dissociation constant $K_d=0.14$ mM found for the binding in solution (Schwartz et al., *J. Biol. Chem.*, 268:766(1993)). This example demonstrates, that dissociation constant of ligand with protein can be obtained in about 10 min.

Returning back to FIG. 14, MP-induced decrease in tension is seen to be completely reversible, introduction of buffer 1 into well 210 results in increase of tension by $\Delta F_1$ equal to its drop upon addition of MP. Exchanging buffer 1 for buffer 2, containing all the components of buffer 1 except for $MnCl_2$ and $CaCl_2$ results in a considerable decrease of tension. Thus, the mechanochemical effect allows an easy detection of known ability of concanavalin to bind divalent cations (see review of G. N. Reeke et al., *Ann. N.Y. Acad. Sci.* 234:369(1974)). Further proof for that can be seen from the effect of addition of 1 mM EDTA to the buffer 2. This substance capable of strong binding to all polyvalent metal cations removes traces of such cations always present in buffer solutions (in concentration of about $10^{-6}$M) and dissociation of these cations from protein reduces tension still more. EDTA effect is not due to direct binding of EDTA molecules to protein, since further introduction of EDTA-free buffer 2 into well 210 does not affect tension.

Introduction of 10 mM MP dissolved in buffer 2 into well 210 results in reversible drop of tension by $\Delta F_2$, similar to the effect, $\Delta F_1$, in buffer 1. This indicates that removed bivalent cations were not necessary for MP binding. As compared to MP, glucose is known to have much lower ability of binding concanavalin A (Lucy L. S. and Golfstein I. J. *Biochem. Biophys. Acta*, 165:398 (1968)), and this can be easily seen from very small tension changes in response to introduction of 5 mM solution of glucose (Glc) into well 210.

This example illustrates the power of the present invention in discovering ability of proteins to interact with different ligands. In less than 1 hour, using single sample, containing only 1 microgram of protein and using one method of binding detection interaction of concanavalin with 4 different substances was characterized.

EXAMPLE 3

This example illustrates a "dosimeter" mode of operation which becomes possible due to rapid and reproducible mode of sample attachment in the device according to the present invention.

Figure 17:
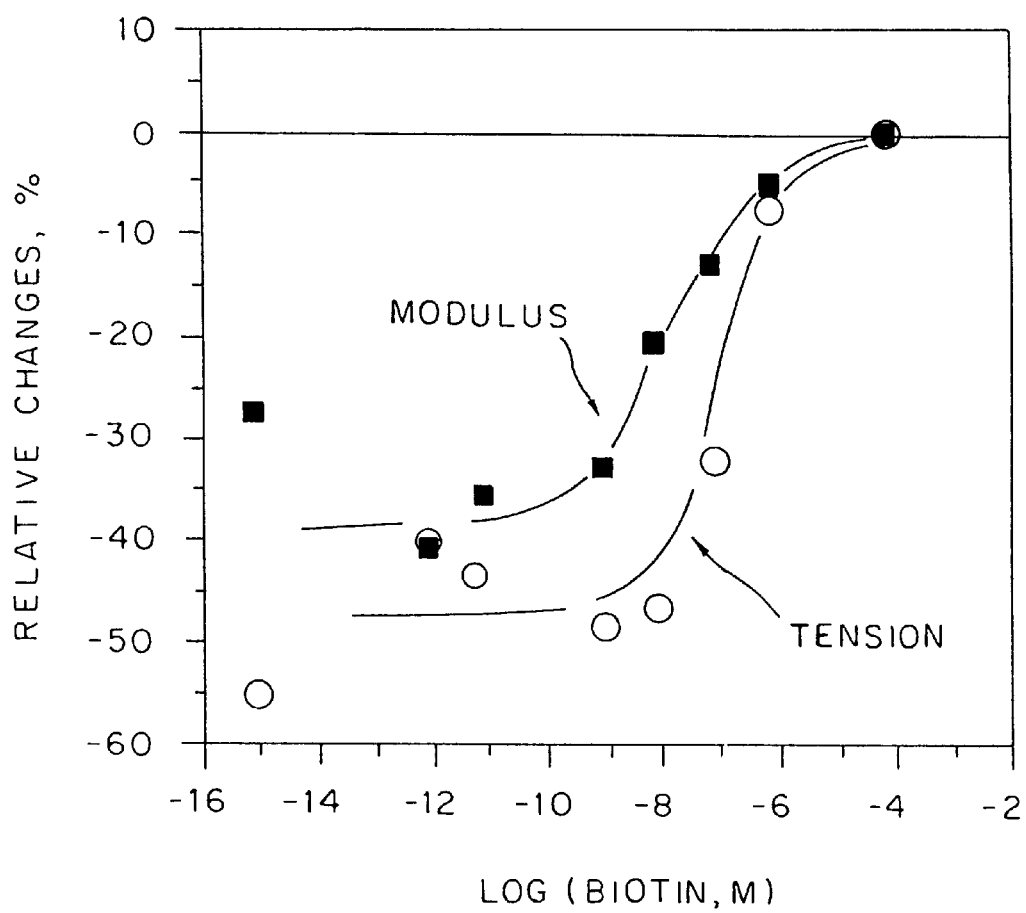
FIG. 17 shows the relative changes in isometric tension and in elastic modulus of avidin films in response to $4 \times 10^{-4}$ M biotin solution measured as shown in FIG. 15. Samples were preexposed to different concentrations of biotin for 48 hours.

In this example, avidin strips were prepared from commercially available protein, (Sigma, St. Louis, Mo.) as described in Example 1 for hexokinase. The strips were placed in solutions of different concentrations of biotin, prepared on 10 mM HEPES buffer, pH=7.5, 0.1 M NaCl. The solutions with strip were shaken for 48 hours at room temperature. After that, strips were attached to the arms 146, 148, stretched, and allowed to relax in the same buffer without biotin as it is presented in FIG. 16. After completion of relaxation, $4\times10^{-4}$ M solution of biotin prepared on the same buffer was introduced into well 210 and changes of isometric tension, $\Delta F$, and modulus were measured. FIG. 17 presents results of such measurements with avidin samples preexposed to different concentrations of biotin. It is seen that (i) all the measurements with each protein sample can be performed in 10–15 min, and (ii) both modulus and tension changes can be used to rapidly characterize the "dose" of ligand obtained by the protein sample, provided it binds the ligand strongly and irreversibly.

EXAMPLE 4

Figure 33A:
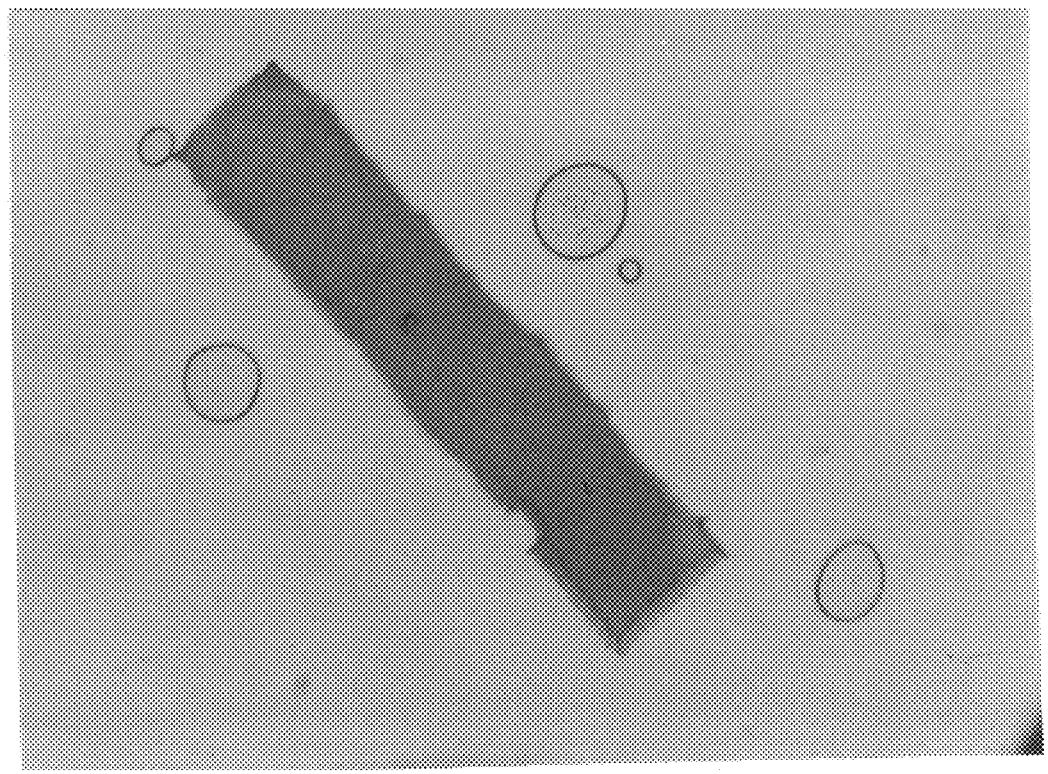
FIGS. 33A and 33B show electrospray fabricated films of concanavalin A (FIG. 33A) and alcohol dehydrogenase from horse liver (FIG. 33B). Protein films were deposited through a single rectangular hole (0.8×0.2 mm) in a mask onto a conducting polymer sublayer film deposited onto an Al electrode.

Protein films were prepared by electrospray for use in a chemical method. A 2 mg/ml concanavalin A (Sigma, St. Louis, Mo.) solution, containing 0.5 mg/ml of glycerol was electrosprayed through a rectangular single hole onto an Al electrode covered with a polymeric conducting sublayer of about 2–5 microns thick. The sublayer was prepared by drying a thin layer of water solution of a mixture of three compounds (polyethylene glycol-8000, poly (anethoesulfonic-Na salt and Triton X-100), 30 each. The protein solution was electrosprayed from a capillary tip placed 20 mm over the substrate, with positive voltage of 4.0 kV at the capillary and a current of 33 nA. Deposition was performed in dry air for 10 minutes. After electrospray deposition, the sample was cross-linked for 15 minutes in a vapor of 250 glutaraldehyde (Aldrich Chemical Company, Milwaukee, Wis.) at 25° C. Upon applying a droplet of water on the substrate surface, the sample was floated off the substrate within 5 seconds. To prepare a microphotograph of the sample, as presented in FIG. 33A, the sample was stained by treatment with a solution of Coomassie brilliant blue R (Sigma, St. Louis, Mo.).

Figure 33B:
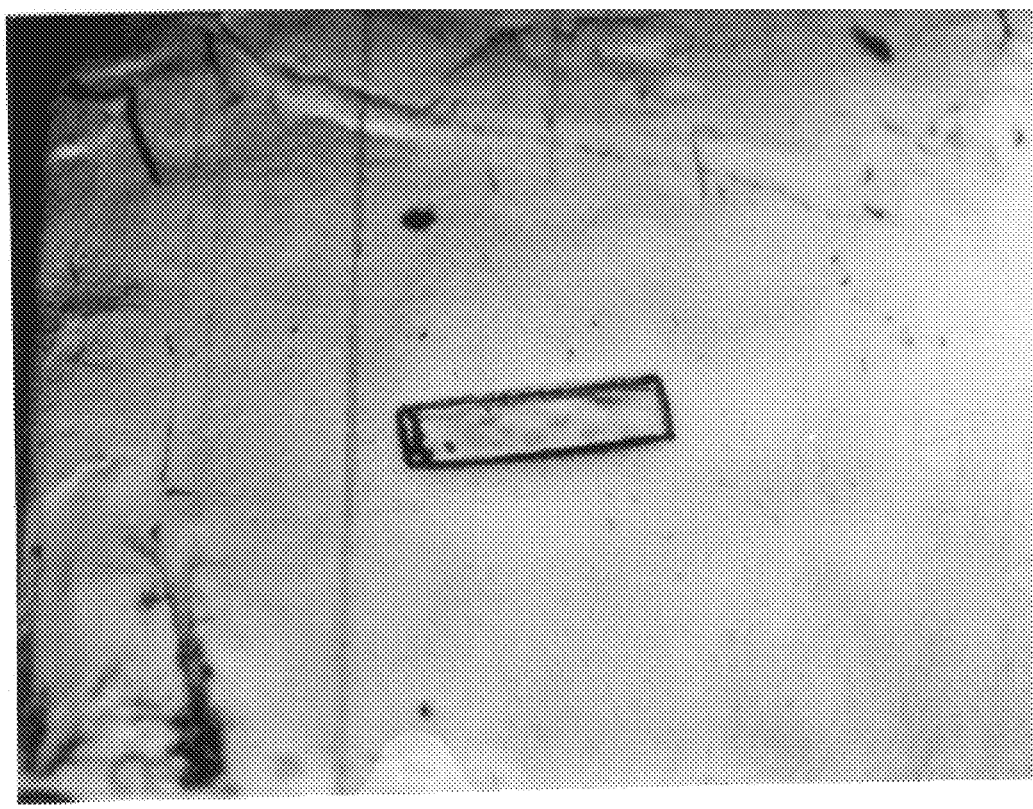

A film of horse liver alcohol dehydrogenase (LADH, Sigma, St. Louis, Mo.), shown in FIG. 33B, was fabricated on an Al electrode covered with a sublayer consisting of 95% of the sodium salt of alginic acid (Sigma, St. Louis, Mo.) and 5% of Triton X-100 detergent. The LADH solution containing 5 mg/ml of protein and 0.15 mg/ml of sucrose was electrosprayed in dry air at +4.3 kV and 30–40 nA from a capillary placed about 15 mm over the substrate. The deposited film was cross-linked for 8 minutes with the vapor from 25% glutaraldehyde at 28° C.

This example demonstrates that small protein samples of a uniform thickness, which is important for testing proteins by a mechanochemical method, can be fabricated by electrospray deposition.

EXAMPLE 5

Figure 34A:
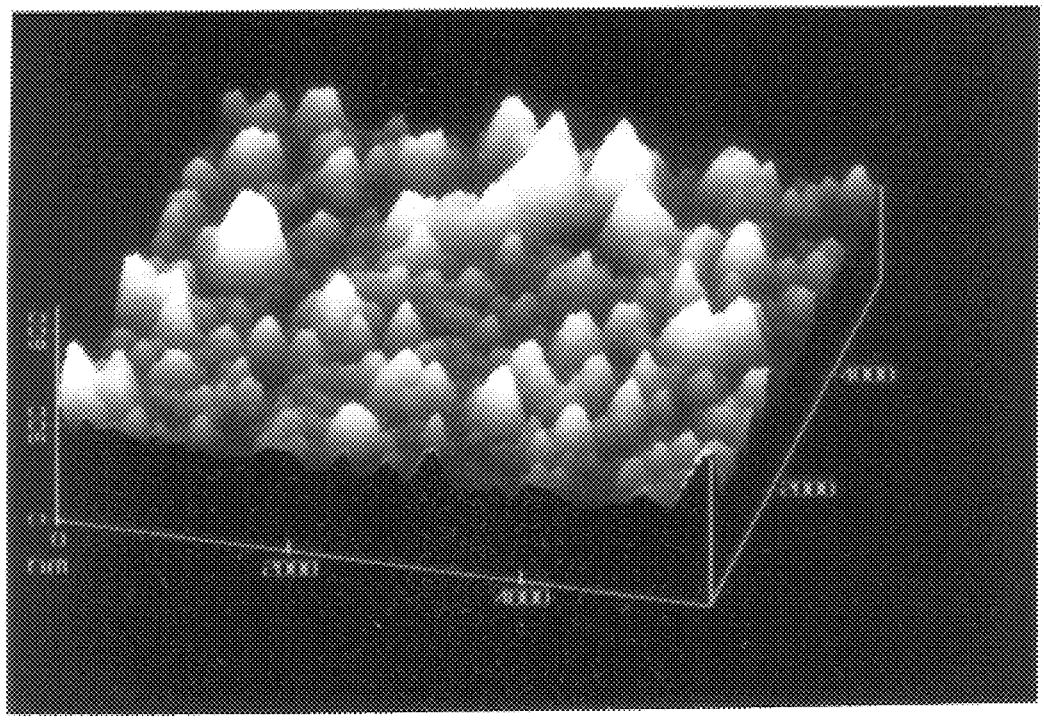
FIGS. 34A and 34B show the porous structure of the electrospray-deposited film of human hemoglobin (image of film surface made by scanning force microscope after dry deposition in FIG. 34A) and changes in film structure as a result of film "baking" (image in FIG. 34B presents the structure of the same film after exposure to wet atmosphere).
Figure 34B:
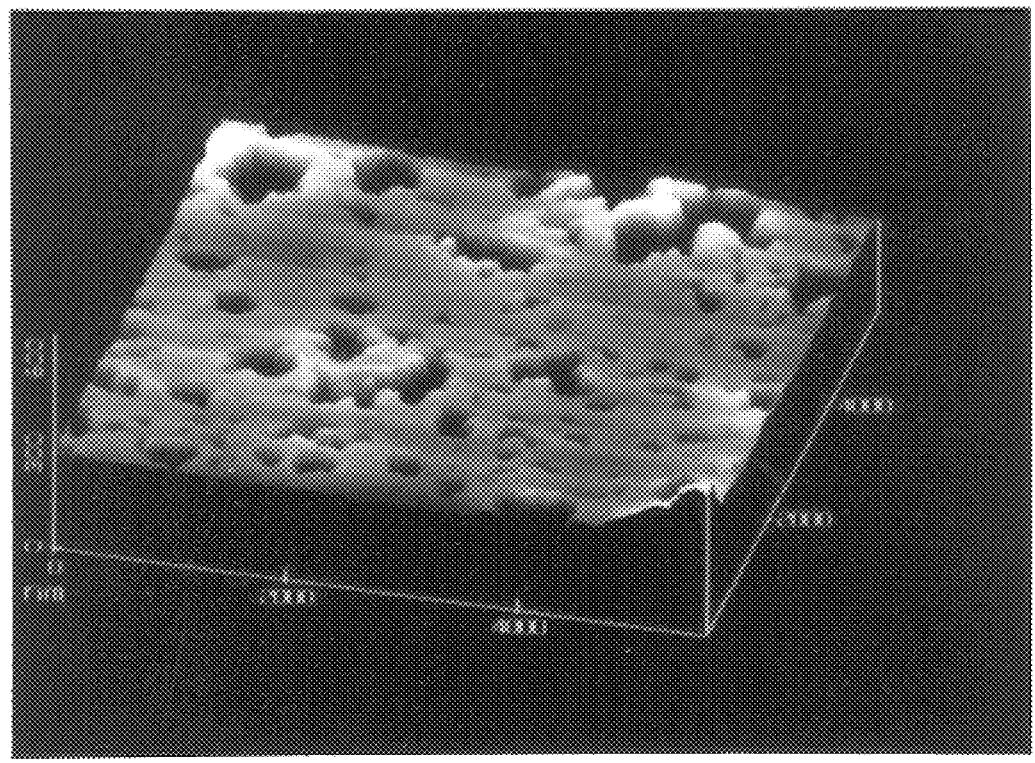

The deposition of protein from concentrated protein solutions in a dry atmosphere results in the formation of a porous structure. FIG. 34A presents an atomic force microscopy (AFM) image of a human hemoglobin film deposited onto a polished gold electrode. The protein was electrosprayed from an aqueous solution containing 0.6 mg/ml human hemoglobin with no other additives added. Deposition was performed in dry air at +5.3 kV on a capillary placed at a distance of about 20 mm over the substrate, with a current of 12 nA and solution flow rate of 100 nl/min. The image presented in FIG. 34A shows the presence of protein clusters with sizes up to about 300 nm. Exposure to humid air (100% relative humidity at room temperature for 20 minutes) resulted in the disappearance of large clusters and the formation of a flat surface with narrow "channels" which are visible as black structures in the image presented in FIG. 34B. This example illustrates the fabrication by electrospray deposition of porous materials from substances which form homogeneous dense films when dried from solution. It also illustrates a means to regulate porosity of electrospray-fabricated films by "baking" in a humid atmosphere, thereby permitting the relative displacement of protein molecules within the clusters.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation

What is claimed is:

1. An apparatus for measurement of the effect of chemicals on a sample film of polymeric material, comprising:

a pair of supporting members, each with a sample-holding tip at one end thereof constructed and adapted to be capable of holding an end of a sample film of polymeric material having a thickness on the order of a micron;

force means, attached to at least one of said supporting members, for applying force to the sample film held by said tips when in use; and measurement means, attached directly or indirectly to the sample film, for measuring changes in a property of the sample film upon being subjected to a chemical when in use.

2. The apparatus in accordance with claim 1, wherein said sample-holding tip capable of pinning the sample film of polymeric material.

3. The apparatus in accordance with claim 1, wherein said sample-holding tip is capable of becoming adhered to the sample film of polymeric material by means of an adhesive.

4. The apparatus in accordance with claim 1, wherein said measurement means comprises means for measuring displacement of one of said supporting members with respect to the other.

5. The apparatus in accordance with claim 1, wherein said measurement means comprises means for measuring the force required to maintain said sample-holding tips at a constant displacement.

6. The apparatus in accordance with claim 1, further including a fluid containment vessel for holding a fluid and immersion means for causing said tips holding the sample film, when in use, to immerse the sample film in the fluid held by said fluid containment vessel, whereby the sample film may be tested while immersed in a fluid in said vessel.

7. The apparatus in accordance with claim 1, further including a sample film holder for presenting the sample film to the sample-holding tips of said supporting members, and alignment means for aligning said sample film holder to a predetermined position relative to said supporting members.

8. The apparatus in accordance with claim 1, wherein said force means comprises means for applying or maintaining force parallel to the direction of the sample film between said sample-holding tips so as to elongate or contract said sample film.

9. The apparatus in accordance with claim 8, wherein said force means further includes means for oscillatingly varying the elongation of the sample film.

10. A method of using the apparatus of claim 1 for the measurement of the effect of chemicals on a sample film of polymeric material, comprising:

affixing a sample film of polymeric material to the sample-holding tips of the pair of supporting members so as to hold the sample film between the tips;

immersing the sample film in a reference fluid;

applying force to the sample film by means of the force means;

measuring a mechanical property of the sample film by means of the measurement means;

immersing the sample film in a fluid containing the chemical to be tested; and remeasuring the same mechanical property of the sample film as was measured in said measuring step, by means of the measurement means;

whereby the effect of the chemical on the polymeric material can be determined by detecting a change in the measured property.

11. The method in accordance with claim 10, wherein said sample holding tip is capable of pinning the sample film of polymeric material, and said affixing step comprises pinning the sample with the tips.

12. The method in accordance with claim 10, wherein said sample-holding tip is capable of becoming adhered to the sample film of polymeric material by means of an adhesive, and said affixing step comprises adhering the sample to the tips by means of an adhesive.

13. The method in accordance with claim 10 for the measurement of ligand binding to a protein or nucleic acid material, wherein said polymeric material comprises a cross-linked protein or nucleic acid material and said chemical is the ligand to be tested for its ability to bind to the protein or nucleic acid material.

14. The method in accordance with claim 13, further including, prior to said affixing step, the steps for preparing the sample film comprising:

forming st rips of a reinforcement material on a surface;

applying a solution of the protein or nucleic acid molecules to be tested onto the surface and in contact with the reinforcement strips thereon;

drying the protein or nucleic acid molecules into a film on the surface and at least partially overlapping the strips of reinforcement material;

cross-linking the protein or nucleic acid molecules of the film; and removing the cross-linked protein or nucleic acid material and the underlying reinforcement strips from the surface, wherein said affixing step comprises affixing the strip of cross-linked protein or DNA material and underlying reinforcement strips to the sample-holding tips such that the sample-holding tips are affixed thereto in the region of the reinforcement strips.

15. A method for preparing a sample film of cross-linked protein or DNA material according to claim 13, comprising the steps of:

electrospraying a solution of protein or nucleic acid molecules onto a surface to form a film;

cross-linking the protein or nucleic molecules in the film; and removing the film of cross-linked protein or nucleic molecules as a sample film.

16. The method in accordance with claim 10, further including, prior to said affixing step, the steps for preparing the sample film comprising:

forming strips of a reinforcement material on a surface;

forming the polymeric material to be tested over the surface including at least a portion of the reinforcement strips so as to adhere to the reinforcement strips; and removing the polymeric material and the reinforcement strips adhered thereto from the surface, wherein said affixing step comprises affixing the polymeric material to the sample-holding tips such that the sample-holding tips are affixed thereto in the region of the reinforcement strips.

17. The method according to claim 16, further comprising the step of pretreating the surface of the strips of reinforcement material to provide adherence to the film of protein or nucleic acid molecules.

18. The method according to claim 16, wherein the reinforcement material is gelatin.

19. The method according to claim 10, wherein (a) said step of applying force to the sample film includes:

stretching the sample film between the supporting members; and allowing the sample film to relax by maintaining a fixed distance between the sample-holding tips until a constant isometric tension of the sample is reached;

(b) said measuring and remeasuring steps comprise measuring the constant isometric tension and/or a spring constant of the sample film; and whereby the change in the measured property includes changes in at least one of the isometric tension and the spring constant.

20. A method for preparing a sample film of cross-linked protein or DNA material, according to claim 19, comprising the steps of:

forming strips or reinforcement material on a surface;

applying a solution of protein or nucleic acid molecules onto the surface and in contact with the reinforcement strips thereon;

drying the protein or nucleic acid molecules into a film on the surface and at least partially overlapping the strips of reinforcement material;

cross-linking the protein or nucleic acid molecules of the film; and removing the cross-linked protein or nucleic acid material and the underlying reinforcement strips from the surface.

21. The method according to claim 20, further comprising the step of pretreating the surface of the strips of reinforcement material to provide adherence to the film of protein or nucleic acid molecules.

22. The method according to claim 20, wherein the reinforcement material is gelatin.

23. An apparatus for measurement of the effect of chemicals on a sample film of polymeric material, comprising:

a pair of supporting members, each with a sample-holding tip at one end thereof, for holding an end of the sample film of polymeric material, wherein both of said sample holding tips anchor the sample film simultaneously;

force means, attached to at least one of said supporting members, for applying force to the sample film held by said tips when in use; and measurement means, attached directly or indirectly to the sample film, for measuring changes in a property of the sample film upon being subjected to a chemical when in use.

24. The apparatus in accordance with claim 23, wherein said sample-holding tip is capable of pinning the sample film of polymeric material.

25. The apparatus in accordance with claim 23, wherein said sample-holding tip is capable of becoming adhered to the sample film of polymeric material by means of an adhesive.

26. The apparatus in accordance with claim 23, wherein said measurement means comprises means for measuring displacement of one of said supporting members with respect to the other.

27. The apparatus in accordance with claim 23, wherein said measurement means comprises means for measuring the force required to maintain said sample-holding tips at a constant displacement.

28. The apparatus in accordance with claim 23, further including a fluid containment vessel for holding a fluid and immersion means for causing said tips holding the sample film, when in use, to immerse the sample film in the fluid held by said fluid containment vessel, whereby the sample film may be tested while immersed in a fluid in said vessel.

29. The apparatus in accordance with claim 23, further including a sample film holder for presenting the sample film to the sample-holding tips of said supporting members, and alignment means for aligning said sample film holder to a predetermined position relative to said supporting members.

30. The apparatus in accordance with claim 23, wherein said force means comprises means for applying or maintaining force parallel to the direction of the sample film between said sample-holding tips so as to elongate or contract said sample film.

31. The apparatus in accordance with claim 30, wherein said force means further includes means for oscillatingly varying the elongation of the sample film.

32. A method of using the apparatus of claim 23, for the measurement of the effect of chemicals on a sample film of polymeric material, comprising:

affixing a sample film of polymeric material to the sample-holding tips of the pair of supporting members so as to hold the sample film between the tips;
immersing the sample film in a reference fluid;
applying force to the sample film by means of the force means;
measuring a mechanical property of the sample film by means of the measurement means;
immersing the sample film in a fluid containing the chemical to be tested; and
remeasuring the same mechanical property of the sample film as was measured in said measuring step, by means of the measurement means;
whereby the effect of the chemical on the polymeric material can be determined by detecting a change in the measured property.

33. The method in accordance with claim 32, wherein said sample holding tip is capable of pinning the sample film of polymeric material, and said affixing step comprising pinning the sample with the tips.

34. The method in accordance with claim 32, wherein said sample-holding tip is capable of becoming adhered to the sample film of polymeric material by means of an adhesive, and said affixing step comprises adhering the sample to the tips by means of an adhesive.

35. The method according to claim 32, wherein
(a) said step of applying force to the sample film includes:
stretching the sample film between the supporting members; and
allowing the sample film to relax by maintaining a fixed distance between the sample-holding tips until a constant isometric tension of the sample is reached;
(b) said measuring and remeasuring steps comprise measuring the constant isometric tension and/or a spring constant of the sample film; and
whereby the change in the measured property includes changes in at least one of the isometric tension and the spring constant.

36. A method for preparing a sample film of cross-linked protein or DNA material, according to claim 35, comprising the steps of:
forming strips or reinforcement material on a surface;
applying a solution of protein or nucleic acid molecules onto the surface and in contact with the reinforcement strips thereon;
drying the protein or nucleic acid molecules into a film on the surface and at least partially overlapping the strips of reinforcement material;
cross-linking the protein or nucleic acid molecules of the film; and
removing the cross-linked protein or nucleic acid material and the underlying reinforcement strips from the surface.

37. The method according to claim 36, further comprising the step of pretreating the surface of the strips of reinforcement material to provide adherence to the film of protein or nucleic acid molecules.

38. The method according to claim 36, wherein the reinforcement material is gelatin.

39. The method in accordance with claim 32, for the measurement of ligand binding to a protein or nucleic acid material, wherein said polymeric material comprises a cross-linked protein or nucleic acid material and said chemical is the ligand to be tested for its ability to bind to the protein or nucleic acid material.

40. The method in accordance with claim 39, further including, prior to said affixing step, the steps for preparing the sample film comprising:
forming strips of a reinforcement material on a surface;
applying a solution of the protein or nucleic acid molecules to be tested onto the surface and in contact with the reinforcement strips thereon;
drying the protein or nucleic acid molecules into a film on the surface and at least partially overlapping the strips of reinforcement material;
cross-linking the protein or nucleic acid molecules of the film; and
removing the cross-linked protein or nucleic acid material and the underlying reinforcement strips form the surface,
wherein said affixing step comprises affixing the strip of cross-linked protein or DNA material and underlying reinforcement strips to the sample-holding tips such that the sample-holding tips are affixed thereto in the region of the reinforcement strips.

41. A method for preparing a sample film of cross-linked protein or DNA material according to claim 39, comprising the steps of:
electrospraying a solution of protein or nucleic acid molecules onto a surface to form a film;
cross-linking the protein or nucleic molecules in the film; and
removing the film of cross-linked protein or nucleic molecules as a sample film.

42. The method in accordance with claim 32, further including, prior to said affixing step, the steps for preparing the sample film comprising:
forming strips of a reinforcement material on a surface;
forming the polymeric material to be tested over the surface including at least a portion of the reinforcement strips so as to adhere to the reinforcement strips; and
removing the polymeric material and the reinforcement strips adhered thereto from the surface,
wherein said affixing step comprises affixing the polymeric material to the sample-holding tips such that the sample-holding tips are affixed thereto in the region of the reinforcement strips.

43. The method according to claim 42, further comprising the step of pretreating the surface of the strips of reinforcement material to provide adherence to the film of protein or nucleic acid molecules.

44. The method according to claim 42, wherein the reinforcement material is gelatin.

* * * * *